(12) United States Patent
Pfaltz et al.

(10) Patent No.: US 8,008,529 B2
(45) Date of Patent: Aug. 30, 2011

(54) CHIRAL LIGANDS USED IN TRANSITION METAL CATALYSTS FOR ASYMMETRIC ADDITION REACTIONS ESPECIALLY HYDROGENATION

(75) Inventors: Andreas Pfaltz, Binningen (CH); Yann Ribourdouille, Kembs (FR); Xiangdong Feng, Qingdao (CN); Balamurugan Ramalingam, Jeyankondam (IN); Benoît Pugin, Münchenstein (CH); Felix Spindler, Starrkirch-Wil (CH)

(73) Assignee: Solvias AG, Basel (CH)

( * ) Notice: Subject to any disclaimer, the term of this patent is extended or adjusted under 35 U.S.C. 154(b) by 322 days.

(21) Appl. No.: 12/227,574

(22) PCT Filed: May 23, 2007

(86) PCT No.: PCT/EP2007/055026
§ 371 (c)(1),
(2), (4) Date: Nov. 21, 2008

(87) PCT Pub. No.: WO2007/135179
PCT Pub. Date: Nov. 29, 2007

(65) Prior Publication Data
US 2009/0171114 A1 Jul. 2, 2009

(30) Foreign Application Priority Data
May 23, 2006 (CH) ...................................... 0831/06

(51) Int. Cl.
*C07F 15/02* (2006.01)
*C07F 9/53* (2006.01)
*C07C 69/34* (2006.01)
*B01J 31/18* (2006.01)

(52) U.S. Cl. ............ 568/14; 556/21; 560/190; 502/162; 502/166; 502/167

(58) Field of Classification Search .................... 568/14; 556/21; 502/162, 166, 167
See application file for complete search history.

(56) References Cited

U.S. PATENT DOCUMENTS
2006/0241315 A1 10/2006 Spindler et al.
2007/0142655 A1 6/2007 Lotz et al.
2007/0161762 A1 7/2007 Chen et al.

FOREIGN PATENT DOCUMENTS
| WO | 00/21663 | 4/2000 |
|---|---|---|
| WO | 2004/099226 | 11/2004 |
| WO | 2005/056568 | 6/2005 |
| WO | 2005/068477 | 7/2005 |
| WO | 2006/003195 | 1/2006 |

OTHER PUBLICATIONS

International Search Report issued Oct. 25, 2007 in the International (PCT) Application PCT/EP2007/055026 of which the present application is the U.S. National Stage.
Written Opinion issued Oct. 25, 2007 in the International (PCT) Application PCT/EP2007/055026 of which the present application is the U.S. National Stage.
Xiao-bin Jiang et al., "The application of monodentate secondary phosphine oxide ligands in rhodium- and iridium-catalyzed asymmetric hydrogenation", Tetrahedron: Asymmetry, vol. 15, No. 14, pp. 2223-2229, XP004523712, ISSN: 0957-4166, Jul. 26, 2004.
P. Gary Eller et al., "Syntheses of New Tetrafluoroaryl Derivatives of Phosphorus and Sulfur", Journal of Organometallic Chemistry, vol. 22, No. 3, pp. 631-636, XP009090293, ISSN: 0022-328X, May 1970.
Xiao-bin Jiang et al., "Application of Monodentate Secondary Phosphine Oxides, a New Class of Chiral Ligands, in Ir(I)-Catalyzed Asymmetric Imine Hydrogenation", Organic Letters, vol. 5, No. 9, pp. 1503-1506, XP009090287, ISSN: 1523-7060, May 1, 2003.
X. Jiang, "Monodentate secondary phosphine oxides (SPO's), Synthesis and application in asymmetric catalysis", pp. 1-173, XP007903156, 2004.

*Primary Examiner* — Sikarl Witherspoon
(74) *Attorney, Agent, or Firm* — Wenderoth, Lind & Ponack, L.L.P.

(57) ABSTRACT

Ligands of the formula (I) secondary phosphine-Q-P(=O)HR$_1$ (I) in the form of mixtures of diastereomers or pure diastereomers, in which secondary phosphine is a secondary phosphine group with hydrocarbon radicals or heterohydrocarbon radicals as substituents; Q is a bivalent bisaryl or bisheteroaryl radical with an axial chiral centre to which the two phosphorus atoms are bonded in the ortho positions to the bisaryl or bisheteroaryl bridge bond, or Q is a bivalent ferrocenyl radical with a planar chiral centre or without a planar chiral centre, to which the phosphorus atom of the secondary phosphine is bonded directly or via a $C_1$-$C_4$-carbon chain to a cyclopentadienyl ring, the —P*(=O)HR$_1$ group is bonded either on the same cyclopentadienyl ring in ortho position to the bonded secondary phosphine or on the other cyclopentadienyl ring; P* is a chiral phosphorus atom, and R$_1$ is a hydrocarbon radical, a heterohydrocarbon radical or a ferrocenyl radical, where R$_1$ is a ferrocenyl radical with a planar chiral centre when Q is a ferrocenyl radical without a planar chiral centre. Metal complexes of these ligands are homogeneous catalysts for asymmetric addition reactions, particularly hydrogenations.

9 Claims, No Drawings

CHIRAL LIGANDS USED IN TRANSITION METAL CATALYSTS FOR ASYMMETRIC ADDITION REACTIONS ESPECIALLY HYDROGENATION

The present invention relates to ligands having at least two chiral centres and having a backbone which is (a) a chiral aromatic or heteroaromatic atropisomer or (b) an achiral or chiral planar-isomeric metallocene, to which are bonded in each case one —$PR_2$ group and one P-chiral —P(O)HR group, where, in the case of an achiral metallocene as the backbone, the R radical in the —P(O)HR group contains at least one chiral centre; to processes for their preparation; to metal complexes of these bidentate ligands with transition metals; and to the use of the metal complexes in asymmetric syntheses, particularly in hydrogenations with hydrogen of prochiral organic compounds which contain at least one carbon/carbon or carbon/heteroatom double bond.

Metal complexes with chiral ligands have been found to be valuable catalysts in asymmetric syntheses. Those metal complexes with which not only sufficient catalytic activity but also high stereoselectivity can be achieved are of practical use. Without these two properties, there is no scale-up to industrial processes for economic reasons.

To date, it is still not possible to forecast which metal complexes with which ligands under which reaction conditions for which unsaturated substrates give rise to practically usable hydrogenation results with regard to the catalytic activity and stereoselectivity. A multitude of different bidentate ligands has therefore been provided, which may contain chelating groups with oxygen, sulphur, nitrogen and/or phosphorus atoms (see, for example, W. Teng, X. Zhang, Chem. Rev. 2003, 103, 3029-3069). Among these bidentate ligands, P^N and P^P ligands have frequently been found to be useful, particularly when the chelating groups are bonded to aromatics with atropisomerism (bisarenes and bisheteroarenes) or planar isomerism (metallocenes).

In recent times, a monodentate phosphine oxide benzene of the formula A and bidentate ligands of the formula B have also been described [see thesis by Xiaobin Jiang with Prof. J. G. de Vries and Prof. B. L. Fering a, University of Groningen 29 Nov. 2004 (ISBN: 90-367-2144X); Xiaobin Jiang et al., Org. Lett., 5 (2003) 1503-6; and Xiaobin Jiang et al., Tetrahedron: Asymmetry, 15 (2004) 2223-9]:

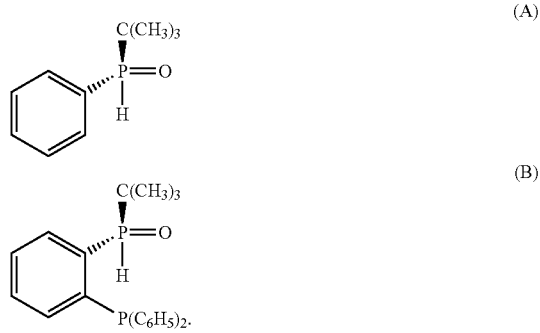

The preparation of these ligands is complicated. The synthesis generally affords racemates which are subsequently separated into their enantiomers, usually with the aid of preparative high-pressure chromatography on chiral columns. This method is very expensive and unsuitable for production on a larger scale. Alternatively, in a few cases, the enantiomers have been separated as an adduct with a chiral auxiliary reagent by selective crystallization. However, this route is too often unsuccessful. Since generally only one of the two enantiomers is required for practical applications, at least half of the desired ligand is also always lost in these methods.

The ligands of the formula A have been used in Ir and Rh complexes for the asymmetric hydrogenation of prochiral imines and alkenes, and good stereo-selectivities but low catalyst activities [turnover frequency (TOF)<3 h$^{-1}$] are observed. The ligands of the formula B have likewise been used in Ir and Rh complexes for the asymmetric hydrogenation of prochiral imines and alkenes, but only low stereoselectivities and very low catalyst activities (TOF<1 h$^{-1}$) have been observed.

There is a great need for further ligands which have a secondary phosphine and phosphine oxide group bonded on the backbone, which can be prepared in a simple manner and which are also suitable as ligands for metal complexes in asymmetric catalysts.

It has now been found that, surprisingly, the preparation of optically pure isomers with a secondary —P(O)HR group bonded on the backbone and a —$PR_2$ group bonded on the backbone, optionally via carbon atoms, succeeds in a particularly simple manner when the backbone is an aromatic with axial chirality, or the ligand contains at least one chiral metallocene. The presence of a further optical centre as well as the chiral secondary phosphine oxide group leads, in the synthesis of the bidentate ligands, often to excellent diastereoselectivities and additionally allows simple purification or separation of the stereoisomers by crystallization or by preparative chromatography on achiral columns.

It has also been found that, surprisingly, these ligands have an unexpectedly great influence on the catalytic properties and, compared to the known ligand B in metal complexes, frequently feature surprisingly high catalytic activities as catalysts, and, depending on the prochiral substrate, very good to very high stereoselectivities can also be achieved.

The invention firstly provides compounds of the formula I having at least two chiral centres in the form of mixtures of diastereomers or pure diastereomers $$\text{secondary phosphine-Q-P*}(=O)HR_1 \qquad (I),$$

in which
secondary phosphine is a secondary phosphine group with hydrocarbon radicals or heterohydrocarbon radicals as substituents;
Q is a bivalent bisaryl or bisheteroaryl radical with an axial chiral centre to which the two phosphorus atoms are bonded in the ortho positions to the bisaryl or bisheteroaryl bridge bond, or Q is a bivalent ferrocenyl radical with a planar chiral centre or without a planar chiral centre, to which the phosphorus atom of the secondary phosphine is bonded directly or via a $C_1$-$C_4$-carbon chain to a cyclopentadienyl ring,
the —P*(=O)HR$_1$ group is bonded either on the same cyclopentadienyl ring in ortho position to the bonded secondary phosphine or on the other cyclopentadienyl ring;
P* is a chiral phosphorus atom, and
R$_1$ is a hydrocarbon radical, a heterohydrocarbon radical or a ferrocenyl radical,
where R$_1$ is a ferrocenyl radical with a planar chiral centre when Q as a ferrocenyl radical does not have a planar chiral centre.

In the context of the present invention, a "chiral centre" can be a planar chiral centre, an axial chiral centre or an atom-centred chiral centre, in which case the atom is preferably C or P.

The compounds of the formula I have usually 2 to 5, preferably 2 to 4 and more preferably 2 or 3 chiral centres.

The compounds of the formula I may, for example, in substituents of the aromatic radicals, in substituents on the cyclopentadienyl in the ferrocene or in the $C_1$-$C_4$-carbon chain, contain at least one asymmetric carbon atom as a further chiral centre.

For explanation, it is noted that the compounds of the formula I also include the tautomeric form in which the —P*(=O)HR$_1$ group is represented as the hydroxyl form —P*(OH)R$_1$. In the two tautomeric forms, the phosphorus atom is asymmetric and chiral.

The bridging group Q may be unsubstituted or substituted by substituents Rx such as halogen or a hydrocarbon radical bonded via a carbon atom, oxygen atom, sulphur atom or silicon atom, for example one to six times, preferably one to four times and more preferably once to twice, where hydrocarbon radicals in substituents $R_x$ may in turn be substituted. When the bridging group Q is a bisaryl or bisheteroaryl radical, it can also be provided with ring-bonding substituents, for example alkylene, alkenylene, alkdienylene, alkylenediamino or alkylenedioxy. When at least two substituents are bonded in the Q group, they may be the same or different.

The optionally substituted substituent $R_x$ may, for example, be $C_1$-$C_{12}$-alkyl, preferably $C_1$-$C_8$-alkyl, and, more preferably $C_1$-$C_4$-alkyl. Examples are methyl, ethyl, n- or i-propyl, n-, i- or t-butyl, pentyl, hexyl, octyl, decyl, undecyl and dodecyl.

The optionally substituted substituent $R_x$ may, for example, be $C_5$-$C_8$-cycloalkyl, preferably $C_5$-$C_6$-cycloalkyl. Examples are cyclopentyl, cyclohexyl and cyclooctyl. The optionally substituted substituent $R_x$ may, for example, be $C_5$-$C_8$-cycloalkylalkyl, preferably $C_5$-$C_6$-cycloalkylalkyl. Examples are cyclopentylmethyl, cyclohexylmethyl or -ethyl and cyclooctylmethyl.

The optionally substituted substituent $R_x$ may, for example, be $C_6$-$C_{18}$-aryl and preferably $C_6$-$C_{10}$-aryl. Examples are phenyl or naphthyl.

The optionally substituted substituent $R_x$ may, for example, be $C_7$-$C_{12}$-aralkyl (for example benzyl or 1-phenyleth-2-yl).

The optionally substituted substituent $R_x$ may, for example, be tri($C_1$-$C_4$-alkyl)Si or triphenylsilyl. Examples of trialkylsilyl are trimethyl-, triethyl-, tri-n-propyl-, tri-n-butyl- and dimethyl-t-butylsilyl.

The substituent $R_x$ may, for example, be halogen. Examples are F, Cl and Br.

The optionally substituted substituent $R_x$ may, for example, be an alkoxy radical, thio radical, sulphoxide or a sulphone radical of the formulae —OR$_{05}$, —SR$_{05}$, —S(O)R$_{05}$ and —S(O)$_2$R$_{05}$, in which R$_{05}$ is $C_1$-$C_{12}$-alkyl, preferably $C_1$-$C_8$-alkyl and more preferably $C_1$-$C_4$-alkyl; $C_5$-$C_8$-cycloalkyl, preferably $C_5$-$C_6$-cycloalkyl; $C_6$-$C_{18}$-aryl and preferably $C_6$-$C_{10}$-aryl; or $C_7$-$C_{12}$-aralkyl. Examples of these hydrocarbon radicals have already been mentioned above for the substituents.

The substituent $R_x$ may, for example, be —CH(O), —C(O)—$C_1$-$C_4$-alkyl or —C(O)—$C_6$-$C_{10}$-aryl.

The optionally substituted substituent $R_x$ may, for example, be —CO$_2$R$_{03}$ or —C(O)—NR$_{01}$R$_{02}$ radicals in which R$_{01}$, R$_{02}$ and R$_{03}$ are each independently $C_1$-$C_{12}$-alkyl, $C_5$-$C_6$-cycloalkyl, $C_5$-$C_6$-cycloalkylmethyl or -ethyl, unsubstituted or $C_1$-$C_4$-alkyl- or $C_1$-$C_4$-alkoxy-substituted $C_6$-$C_{10}$-aryl or $C_7$-$C_{12}$-aralkyl, or R$_{01}$ and R$_{02}$ together are trimethylene, tetramethylene, 3-oxa-1,5-pentylene or 3-($C_1$-$C_4$-alkyl)amino-1,5-pentylene. R$_{01}$, R$_{02}$ and R$_{03}$ may, as alkyl, be linear or branched, and the alkyl contains preferably 1 to 8 and more preferably 1 to 4 carbon atoms. R$_{01}$, R$_{02}$ and R$_{03}$ may, as aryl, for example, be phenyl or naphthyl and, as aralkyl, be benzyl or phenylethyl. Some examples of R$_{01}$, R$_{02}$ and R$_{03}$ are methyl, ethyl, n- or i-propyl, n-, i- or t-butyl, pentyl, hexyl, heptyl, octyl, nonyl, decyl, undecyl, dodecyl, phenyl, benzyl, methylphenyl, methylbenzyl, methoxyphenyl, dimethoxyphenyl and methoxybenzyl.

The optionally substituted substituent $R_x$ may, for example, be —S(O)O—R$_{03}$, —S(O)$_2$—O—R$_{03}$, —S(O)—NR$_{01}$R$_{02}$ and —S(O)$_2$—NR$_{01}$R$_{02}$ radicals, in which R$_{01}$, R$_{02}$ and R$_{03}$ are each as defined above, including the preferences.

When Q is the bivalent radical of a bisaryl or bisheteroaryl with monocyclic aromatics, preferably one or both of the other ortho positions to the bond (bridge bond) which joins the two monocyclic aromatics are substituted in order to prevent free rotation. In this case, preferred substituents are $C_1$-$C_{12}$-alkyl, preferably $C_1$-$C_8$-alkyl and more preferably $C_1$-$C_4$-alkyl; $C_5$-$C_8$-cycloalkyl, preferably $C_5$-$C_6$-cycloalkyl; $C_6$-$C_{18}$-aryl and preferably $C_6$-$C_{10}$-aryl; or $C_7$-$C_{12}$-aralkyl; $C_1$-$C_{12}$-alkoxy, preferably $C_1$-$C_8$-alkoxy and more preferably $C_1$-$C_4$-alkoxy; $C_5$-$C_8$-cycloalkoxy, preferably $C_5$-$C_6$-cycloalkoxy; $C_6$-$C_{18}$-aryloxy and preferably $C_6$-$C_{10}$-aryloxy; or $C_7$-$C_{12}$-aralkyloxy; $C_1$-$C_{12}$-alkylthio, preferably $C_1$-$C_8$-alkylthio and more preferably $C_1$-$C_4$-alkylthio; $C_5$-$C_8$-cycloalkylthio, preferably $C_5$-$C_6$-cycloalkylthio; $C_6$-$C_{18}$-arythiol and preferably $C_6$-$C_{10}$-arylthio; or $C_7$-$C_{12}$-aralkylthio, and tri-$C_1$-$C_8$-alkylsilyl.

When Q is the bivalent radical of a bisaryl or bisheteroaryl with monocyclic aromatics, it is also possible for bivalent substituents to be bonded, in the case of bisaryls to two adjacent carbon atoms, particularly in the 5,6 and/or 5',6' positions (fused rings) or in the 6,6' positions. The bivalent substituents may be ω,ω'-$C_1$- to —$C_6$-alkylene, $C_1$- to —$C_6$-alkylene-O—, $C_1$- to —$C_6$-alkylene-N($C_1$-$C_4$-alkyl)-, —O—($C_1$- to —$C_6$-alkylene)-O—, —($C_1$-$C_4$-alkyl)N($C_1$- to —$C_6$-alkylene)-N($C_1$-$C_4$-alkyl)-, —O—($C_1$- to —$C_6$-alkylene)-N($C_1$-$C_4$-alkyl)-, —CH$_2$—CH=CH—, —O—CH=CH—, —S—CH=CH—, —N($C_1$-$C_4$-alkyl)-CH=CH—, —CH=CH—CH=CH—, —CH=CH—CH=N—, —CH=CH—N=CH—, —CH=N—CH=CH—, —N=CH—CH=CH—, —CH=N—CH=N—, —N=CH—CH=N—, and —CH=N—N=CH—.

The hydrocarbon radicals of the substituents $R_x$ may in turn be mono- or polysubstituted, for example mono- to trisubstituted, preferably mono- or disubstituted, for example by halogen (F, Cl or Br, particularly F), —OH, —SH, —CH(O), —CN, —NR$_{001}$R$_{02}$, —C(O)—O—R$_{003}$, —S(O)—O—R$_{003}$, —S(O)$_2$—O—R$_{003}$, —P(OR$_{03}$)$_2$, —P(O)(OR$_{003}$)$_2$, —C(O)—NR$_{001}$R$_{002}$, —S(O)—NR$_{001}$R$_{02}$, —S(O)$_2$—NR$_{001}$R$_{002}$, —O—(O)C—R$_{004}$, —R$_{001}$N—(O)C—R$_{004}$, —R$_{001}$N—S(O)—R$_{004}$, —R$_{001}$N—S(O)$_2$—R$_{004}$, $C_1$-$C_4$-alkyl, $C_1$-$C_4$-alkoxy, $C_1$-$C_4$-alkylthio, $C_5$-$C_6$-cycloalkyl, phenyl, benzyl, phenoxy or benzyloxy, where R$_{001}$ and R$_{002}$ are each independently hydrogen, $C_1$-$C_4$-alkyl, cyclopentyl, cyclohexyl, phenyl, benzyl or R$_{001}$ and R$_{002}$ together are tetramethylene, pentamethylene or 3-oxapentane-1,5-diyl, R$_{003}$ is hydrogen, $C_1$-$C_8$-alkyl, $C_5$-$C_6$-cycloalkyl, phenyl or benzyl, and R$_{004}$ is $C_1$-$C_{18}$-alkyl and preferably $C_1$-$C_{12}$-alkyl, $C_1$-$C_4$-haloalkyl, $C_1$-$C_4$-hydroxyalkyl, $C_5$-$C_8$-cycloalkyl (for example cyclopentyl, cyclohexyl), $C_6$-$C_{10}$-aryl (for example phenyl or naphthyl) or $C_7$-$C_{12}$-aralkyl (for example benzyl).

The bivalent Q radical in formula I may be radicals in which two hydrocarbon aromatics, two heteroaromatics or one hydrocarbon aromatic and one heteroaromatic are bonded to one another. In fused heteroaromatics with five-membered heteroaromatic rings, the heteroaromatic rings and preferably the hydrocarbon rings may be joined. Examples of hydrocarbon aromatics are in particular benzene, indene and naphthalene. Examples of heteroaromatics and fused heteroaromatics are furan, benzofuran, thiophene, benzothiophene, N—(C$_1$-C$_4$-alkyl)pyrrole, N(C$_1$-C$_4$-alkyl) indole, pyridine, quinoline and isoquinoline.

Preferred bivalent Q radicals of bisarylene or -heteroarylene are those of the formulae II and IIa

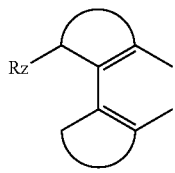

(II)

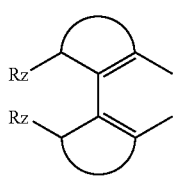

(IIa)

in which one or both Rz are a substituent or part of a fused ring, and the rings together with the carbon atoms bonded to them form optionally fused 5- or 6-membered aromatic or heteroaromatic rings which are unsubstituted or mono- or polysubstituted. In a preferred embodiment of the invention, the bivalent Q radical in formula I, as bisaryl or bishetaroaryl, corresponds to the formulae III, IV, V or VI

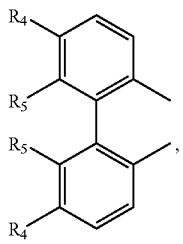

(III)

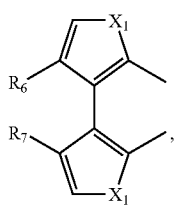

(IV)

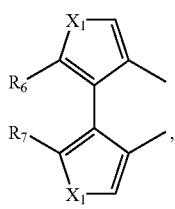

(V)

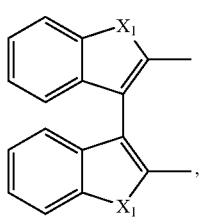

(VI)

in which $X_1$ is O, S or N(C$_1$-C$_4$-alkyl);

$R_4$, $R_5$, $R_6$ and $R_7$ are each independently hydrogen, C$_1$-C$_8$-alkyl, C$_5$-C$_8$-cycloalkyl, C$_1$-C$_8$-alkoxy, C$_1$-C$_8$-alkylthio, C$_1$-C$_8$-hydroxyalkyl, C$_2$-C$_8$-hydroxyalkoxy, C$_1$-C$_8$-alkoxy-C$_1$-C$_8$-alkyl, C$_1$-C$_4$-alkoxy-C$_1$-C$_8$-alkoxy, C$_6$-C$_{10}$-aryl, C$_7$-C$_{12}$-aralkyl, —OCF$_3$ or —CF$_3$, where at least one of $R_5$ is a substituent, or $R_4$ and $R_5$ together are trimethylene, tetramethylene, —CH$_2$—CH═CH—, —CH═CH—CH═CH—, —O—CH═CH—, —S—CH═CH—, —N(C$_1$-C$_4$-alkyl)-CH═CH—, —O—CH$_2$—O—, —O—CF$_2$—O—, —O—CH$_2$—CH$_2$—O—, —N(C$_1$-C$_4$-alkyl)-CH$_2$—CH$_2$—O—, or the R$_5$ radicals together are C$_1$-C$_6$-alkylene or —O—(C$_1$-C$_6$-alkylene)-O—. In the bivalent radicals of the formulae III, IV, V and VI, further hydrogen atoms may be substituted, for example by radicals as defined for R$_4$, R$_5$, R$_6$ and R$_7$.

The aromatic and heteroaromatic rings may contain further substituents as defined above.

A preferred subgroup is that of compounds of the formula III in which R$_5$ is C$_1$-C$_4$-alkyl (for example methyl, ethyl, n- and i-propyl, n-, i- and t-butyl), C$_1$-C$_4$-alkoxy (for example methoxy, ethoxy, n- or i-propoxy, butoxy), C$_1$-C$_4$-hydroxyalkyl (for example hydroxymethyl, hydroxyethyl), C$_2$-C$_4$-hydroxyalkoxy (for example hydroxyethyloxy, hydroxypropyloxy), C$_1$-C$_4$-alkoxy-C$_1$-C$_2$-alkyl (for example methoxymethyl, ethoxymethyl, methoxyethyl, ethoxyethyl), C$_1$-C$_4$-alkoxy-C$_1$-C$_2$-alkoxy (for example methoxymethoxy, methoxyethoxy, ethoxymethoxy), trifluoromethyl or trimethylsilyl; R$_4$ and R$_5$ together are trimethylene, tetramethylene, —CH$_2$—CH═CH—, —CH═CH—CH═CH—, —O—CH$_2$—O—, —O—CF$_2$—O—, —O—CH$_2$—CH$_2$—O—, —N(C$_1$-C$_4$-alkyl)-CH$_2$—CH$_2$—O— or benzene-1,2-dioxy, or the R$_5$ radicals together are C$_2$-C$_6$-alkylene, —O—(C$_1$-C$_4$-alkylene)-O— or —O—CF$_2$—O—.

In another preferred embodiment of the invention, the bivalent Q radical in formula I, as a ferrocenyl radical with a planar chiral centre, corresponds to the radicals of the formulae VII, VIII and IX

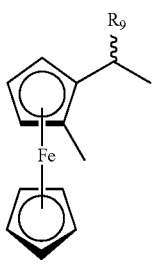

(VII)

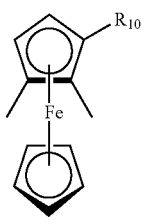

(VIII)

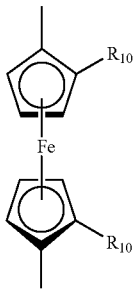
(IX)

or a ferrocenyl radical without a planar chiral centre of the formula XX

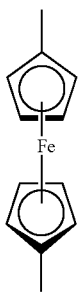
(XX)

in which
$R_9$ is $C_1$-$C_8$-alkyl, $C_5$-$C_8$-cycloalkyl, phenyl, benzyl or methylbenzyl;
$R_{10}$ is vinyl, methyl, ethyl, a C-bonded chiral group which directs metals of metallating reagents into the ortho position, or $R_{10}$ is a —$CH_2$—$NR_{11}R_{12}$ group;
$R_9$ is preferably $C_1$-$C_4$-alkyl, cyclopentyl, cyclohexyl, phenyl, benzyl or methylbenzyl; or
$R_{11}$ and $R_{12}$ are each independently $C_1$-$C_8$-alkyl, $C_5$-$C_8$-cycloalkyl, $C_6$-$C_{10}$-aryl, $C_7$-$C_{12}$-aralkyl, $C_7$-$C_{12}$-alkaryl, or $C_{8-12}$-alkaralkyl, or $R_1$ and $R_{12}$ together are tetramethylene, pentamethylene or 3-oxapentane-1,5-diyl.
$R_9$ is more preferably methyl, ethyl or phenyl.
$R_{11}$ and $R_{12}$ are preferably identical radicals. $R_{11}$ and $R_{12}$ are preferably each $C_1$-$C_4$-alkyl, cyclopentyl, cyclohexyl, phenyl, methylphenyl, methylbenzyl or benzyl, or $R_1$, and $R_{12}$ together are preferably tetramethylene or 3-oxapentane-1,5-diyl. More preferably, $R_{11}$ and $R_{12}$ are each methyl or ethyl.
In the ortho-directing chiral $R_{10}$ group, the chiral atom is preferably bonded in the 1, 2 or 3 position to the cyclopentadienyl-$R_{10}$ bond. The $R_{10}$ group may be open-chain radicals or cyclic radicals, the atoms being selected from the group of H, C, O, S and N.
The $R_{10}$ group may, for example, correspond to the formula —HC*$R_{14}R_{15}$ (* indicates the asymmetric atom) in which $R_{14}$ is $C_1$-$C_8$-alkyl, $C_5$-$C_8$-cycloalkyl (cyclohexyl), $C_6$-$C_{10}$-aryl (phenyl), $C_7$-$C_{12}$-aralkyl (benzyl) or $C_7$-$C_{12}$-alkaralkyl (methylbenzyl), $R_{15}$ is —$OR_{16}$ or —$NR_{11}R_{12}$, $R_{16}$ is $C_1$-$C_8$-alkyl, $C_5$-$C_8$-cycloalkyl, phenyl or benzyl, and $R_{11}$ and $R_{12}$ are the same or different and are each $C_1$-$C_8$-alkyl, $C_5$-$C_8$-cycloalkyl, phenyl or benzyl, or $R_{11}$ and $R_{12}$ together with the nitrogen atom form a five- to eight-membered ring. $R_{14}$ is preferably $C_1$-$C_6$-alkyl, for example methyl, ethyl, n-propyl, or phenyl. $R_{16}$ is preferably $C_1$-$C_4$-alkyl, for example methyl, ethyl, n-propyl and n- or i-butyl. $R_{11}$ and $R_{12}$ are preferably identical radicals and are preferably each $C_1$-$C_4$-alkyl, for example methyl, ethyl, n-propyl, i-propyl and n- or i-butyl, and together tetramethylene, pentamethylene or 3-oxa-1,5-pentylene. Particularly preferred groups of the formula —$HCR_{14}R_{15}$ are 1-methoxyeth-1-yl, 1-dimethylaminoeth-1-yl and 1-(di methylamino)-1-phenylmethyl.

When $R_{10}$ is a radical without a chiral α-carbon atom, it is bonded to the cyclopentadienyl ring via a carbon atom either directly or via a bridge group. The bridge group may, for example, be methylene, ethylene or an imine group. Cyclic radicals bonded to the bridge group are preferably saturated and are more preferably $C_1$-$C_4$-alkyl-, ($C_1$-$C_4$-alkyl)$_2$NCH$_2$—, ($C_1$-$C_4$-alkyl)$_2$NCH$_2$CH$_2$—, $C_1$-$C_4$-alkoxymethyl- or $C_1$-$C_4$-alkoxyethyl-substituted N—, O— or N,O-heterocycloalkyl having a total of 5 or 6 ring atoms. Open-chain radicals are preferably bonded to the cyclopentadienyl ring via a CH$_2$ group and the radicals derive preferably from amino acids or ephedrine. Some preferred examples are:

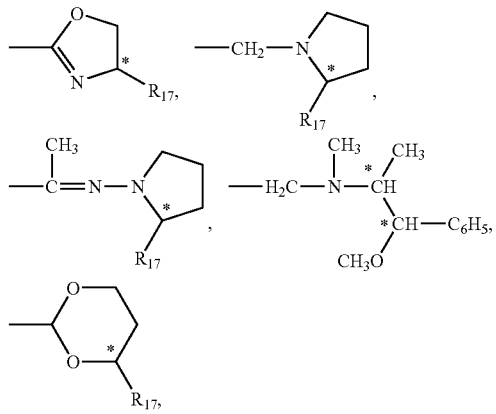

in which $R_{17}$ is $C_1$-$C_4$-alkyl, ($C_1$-$C_4$-alkyl)$_2$NCH$_2$—, ($C_1$-$C_4$-alkyl)$_2$NCH$_2$CH$_2$—, $C_1$-$C_4$-alkoxymethyl or $C_1$-$C_4$-alkoxyethyl. More preferably $R_{17}$ is methoxymethyl or dimethylaminomethyl.

Radicals of the formulae

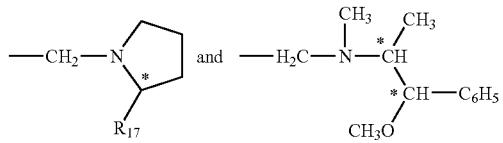

may be converted in a simple manner by means of substitution to preferred —$CH_2$—$NR_{11}R_{12}$ groups.

In a preferred embodiment, $R_{10}$ is —$CH_2$—$NR_{11}R_{12}$, —$CHR_9$—$NR_{11}R_{12}$, vinyl, methyl or ethyl, where $R_9$ is methyl, ethyl or phenyl, and $R_{11}$ and $R_{12}$ are each methyl or ethyl.

The secondary phosphine group may contain two identical or different hydrocarbon radicals or heterohydrocarbon radicals. The secondary phosphine group preferably contains two identical hydrocarbon radicals or heterohydrocarbon radicals.

The hydrocarbon radicals and heterohydrocarbon radicals in the secondary phosphine group may be unsubstituted or substituted and/or contain heteroatoms selected from the group of O, S, —N= or N($C_1$-$C_4$-alkyl). They may contain 1 to 30, preferably 1 to 20 and more preferably 1 to 12 carbon atoms. The hydrocarbon radical may be selected from the group of linear or branched $C_1$-$C_{18}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl, naphthyl, furyl or benzyl; or halogen-, $C_1$-$C_6$-alkyl-, trifluoromethyl-, $C_1$-$C_6$-alkoxy-, trifluoromethoxy-, $(C_6H_5)_3Si$, $(C_1$-$C_{12}$-alkyl$)_3Si$ or secondary amino-substituted phenyl, naphthyl, furyl or benzyl.

Examples of P substituents as alkyl, which preferably contains 1 to 6 carbon atoms, are methyl, ethyl, n-propyl, i-propyl, n-butyl, i-butyl, t-butyl, and the isomers of pentyl and hexyl. Examples of P substituents as optionally alkyl-substituted cycloalkyl are cyclopentyl, cyclohexyl, methyl- and ethylcyclohexyl, and dimethylcyclohexyl. Examples of P substituents as alkyl- and alkoxy-substituted phenyl and benzyl are methylphenyl, dimethylphenyl, trimethylphenyl, ethylphenyl, methylbenzyl, methoxyphenyl, dimethoxyphenyl, trimethoxyphenyl, trifluoromethylphenyl, bis(trifluoromethyl)phenyl, tris(trifluoromethyl)phenyl, trifluoromethoxyphenyl, bis(trifluoromethoxy)phenyl, fluoro- and chlorophenyl and 3,5-dimethyl-4-methoxyphenyl.

Preferred secondary phosphine groups are those which contain identical radicals selected from the group of $C_1$-$C_6$-alkyl, unsubstituted cyclopentyl or cyclohexyl or cyclopentyl or cyclohexyl substituted by 1 to 3 $C_1$-$C_4$-alkyl or $C_1$-$C_4$-alkoxy, benzyl and particularly phenyl, which are unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl.

The secondary phosphine group corresponds preferably to the formula —$PR_2R_3$ in which $R_2$ and $R_3$ are each independently a hydrocarbon radical which has 1 to 18 carbon atoms and is unsubstituted or substituted by $C_1$-$C_6$-alkyl, trifluoromethyl, $C_1$-$C_6$-alkoxy, trifluoromethoxy, $(C_1$-$C_4$-alkyl$)_2$ amino, $(C_6H_5)_3Si$, $(C_1$-$C_{12}$-alkyl$)_3Si$, halogen and/or O heteroatoms.

$R_2$ and $R_3$ are preferably each radicals selected from the group of linear or branched $C_1$-$C_6$-alkyl, unsubstituted cyclopentyl or cyclohexyl or cyclopentyl or cyclohexyl substituted by one to three $C_1$-$C_4$-alkyl or $C_1$-$C_4$-alkoxy, furyl, unsubstituted benzyl or benzyl substituted by one to three $C_1$-$C_4$-alkyl or $C_1$-$C_4$-alkoxy, and in particular unsubstituted phenyl or phenyl substituted by one to three F, Cl, $C_1$-$C_4$-alkyl, $C_1$-$C_4$-alkoxy, $C_1$-$C_4$-fluoroalkyl or $C_1$-$C_4$-fluoroalkoxy.

More preferably, $R_2$ and $R_3$ are each radicals selected from the group of $C_1$-$C_6$-alkyl, cyclopentyl, cyclohexyl, furyl and unsubstituted phenyl or phenyl substituted by one to three F, Cl, $C_1$-$C_4$-alkyl, $C_1$-$C_4$-alkoxy and/or $C_1$-$C_4$-fluoroalkyl.

When $R_2$ and $R_3$ in the —$PR_2R_3$ group are different, the phosphorus atom of the secondary phosphine group is a further chiral centre.

The secondary phosphine group may be cyclic secondary phosphine, for example those of the formulae

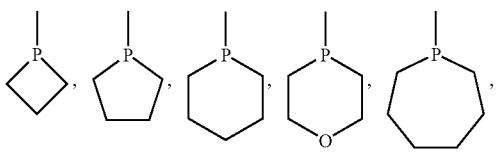

which are unsubstituted or mono- or polysubstituted by $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkyl- or $C_1$-$C_4$-alkoxyphenyl, benzyl, $C_1$-$C_4$-alkyl- or $C_1$-$C_4$-alkoxybenzyl, benzyloxy, $C_1$-$C_4$-alkyl- or $C_1$-$C_4$-alkoxybenzyloxy or $C_1$-$C_4$-alkylidenedioxy.

The substituents may be bonded in one or both α positions to the phosphorus atom in order to introduce chiral carbon atoms. The substituents in one or both α positions are preferably $C_1$-$C_4$-alkyl or benzyl, for example methyl, ethyl, n- or i-propyl, benzyl or —$CH_2$—O—$C_1$-$C_4$-alkyl or —$CH_2$—O—$C_6$-$C_{10}$-aryl.

Substituents in the β,γ positions may, for example, be $C_1$-$C_4$-alkyl, $C_1$-$C_4$-alkoxy, benzyloxy, or —O—$CH_2$—O—, —O—$CH(C_1$-$C_4$-alkyl$)$-O— and —O—$C(C_1$-$C_4$-alkyl$)_2$-O—. Some examples are methyl, ethyl, methoxy, ethoxy, —O—$CH(methyl)$-O— and —O—$C(methyl)_2$-O—.

Depending on the type of substitution, and number of substituents, the cyclic phosphine radicals may be C-chiral, P-chiral or C- and P-chiral.

An aliphatic 5- or 6-membered ring or benzene may be fused onto two adjacent carbon atoms in the radicals of the above formulae.

The cyclic secondary phosphino may, for example, correspond to the formulae (only one of the possible diastereomers is given)

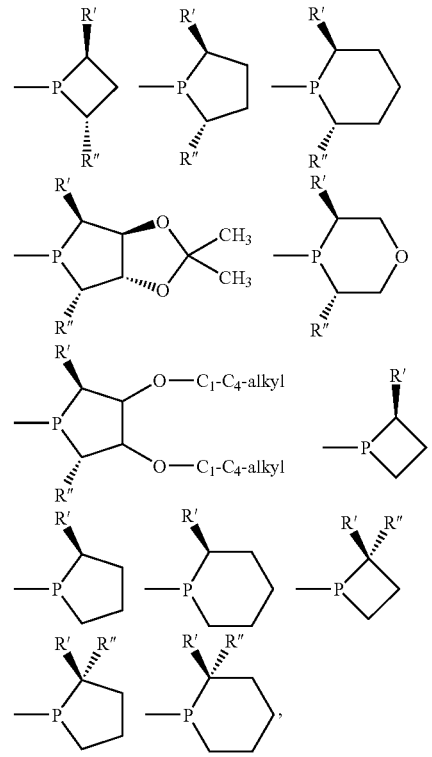

in which
the R' and R" radicals are each $C_1$-$C_4$-alkyl, for example methyl, ethyl, n- or i-propyl, benzyl, or —$CH_2$—O—$C_1$-$C_4$-alkyl or —$CH_2$—O—$C_6$-$C_{10}$-aryl, and R' and R" are identical or different from one another.

In the compounds of the formula I, secondary phosphine is preferably a noncyclic secondary phosphine selected from the group of —$P(C_1$-$C_6$-alkyl$)_2$, —$P(C_5$-$C_8$-cycloalkyl$)_2$, —$P(C_7$-$C_8$-bicycloalkyl$)_2$, —$P(o$-furyl$)_2$, —$P(C_6H_5)_2$, —$P[2$-$(C_1$-$C_6$-alkyl$)C_6H_4]_2$, —$P[3$-$(C_1$-$C_6$-alkyl$)C_6H_4]_2$, —$P[4$-$(C_1$-$C_6$-alkyl$)C_6H_4]_2$, —$P[2$-$(C_1$-$C_6$-alkoxy$)C_6H_4]_2$, —$P[3$-$(C_1$-$C_6$-alkoxy$)C_6H_4]_2$, —$P[4$-$(C_1$-$C_4$-alkoxy$)C_6H_4]_2$, —$P[2$-$(trifluoromethyl)C_6H_4]_2$, —$P[3$-$(trifluoromethyl)C_6H_4]_2$, —$P[4$-$(trifluoromethyl)C_6H_4]_2$, —$P[3,5$-bis$(trifluoromethyl)C_6H_3]_2$, —$P[3,5$-bis$(C_1$-$C_6$-alkyl$)_2C_6H_3]_2$, —$P[3,$ 5-bis($C_1$-$C_6$-alkoxy)$_2$$C_6$$H_3$]$_2$ and —P[3,5-bis($C_1$-$C_6$-alkyl)$_2$-4-($C_1$-$C_6$-alkoxy)$C_6$$H_2$]$_2$, or a cyclic phosphine selected from the group of

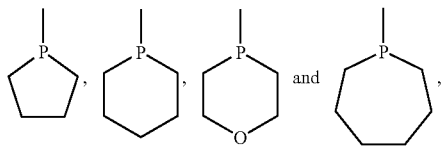

which are unsubstituted or mono- or polysubstituted by $C_1$-$C_4$-alkyl, $C_1$-$C_4$-alkoxy, $C_1$-$C_4$-alkoxy-$C_1$-$C_2$-alkyl, phenyl, benzyl, benzyloxy or $C_1$-$C_4$-alkylidenedioxy.

Some specific examples are —P($CH_3$)$_2$, —P(i-$C_3$$H_7$)$_2$, —P(n-$C_4$$H_9$)$_2$, —P(i-$C_4$$H_9$)$_2$, —P(t-$C_4$$H_9$)$_2$, —P($C_5$$H_9$), —P($C_6$$H_{11}$)$_2$, —P(norbornyl)$_2$, —P(o-furyl)$_2$, —P($C_6$$H_5$)$_2$, P[2-(methyl)$C_6$$H_4$]$_2$, P[3-(methyl)$C_6$$H_4$]$_2$, —P[4-(methyl)$C_6$$H_4$]$_2$, —P[2-(methoxy)$C_6$$H_4$]$_2$, —P[3-(methoxy)$C_6$$H_4$]$_2$, —P[4-(methoxy)$C_6$$H_4$]$_2$, —P[3-(trifluoromethyl)$C_6$$H_4$]$_2$, —P[4-(trifluoromethyl)$C_6$$H_4$]$_2$, —P[3,5-bis(trifluoromethyl)$C_6$$H_3$]$_2$, —P[3,5-bis(methyl)$_2$$C_6$$H_3$]$_2$, —P[3,5-bis(methoxy)$_2$$C_6$$H_3$]$_2$ and —P[3,5-bis(methyl)$_2$-4-(methoxy)$C_6$$H_2$]$_2$, and those of the formulae

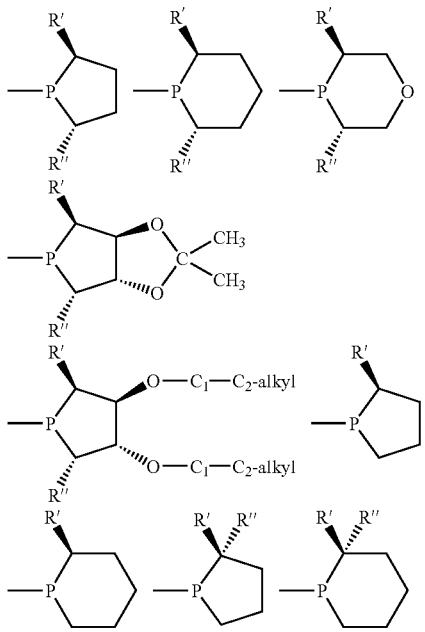

in which
R' is methyl, ethyl, methoxy, ethoxy, phenoxy, benzyloxy, methoxymethyl, ethoxymethyl or benzyloxymethyl and R" independently has the same definition as R' and is different from R'.

The $C_1$-$C_4$-carbon chain to which the secondary phosphine may be bonded is preferably an unsubstituted or $C_1$-$C_6$-alkyl-, benzyl-, phenyl-, cyclopentyl- or cyclohexyl-substituted alkylene group having 1 to 3 and preferably 1 or 2 carbon atoms. The alkylene group preferably corresponds to the formula —CHR$_8$— in which R$_8$ is hydrogen, $C_1$-$C_4$-alkyl, cyclohexyl or phenyl.

When Q is a ferrocene backbone without chirality, R$_1$ must necessarily contain at least one chiral centre. When Q is a ferrocene backbone with chirality, R$_1$ may be chiral.

When R$_1$ is a hydrocarbon radical or a heterohydrocarbon radical, these radicals have the same definitions and preferences as the above-defined substituents in the secondary phosphine group or R$_2$ in the —PR$_2$R$_3$ group. R$_1$ may be selected from the group of linear or branched $C_1$-$C_{18}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-CH$_2$—; phenyl, naphthyl, furyl or benzyl; or halogen-, $C_1$-$C_6$-alkyl-, trifluoromethyl-, $C_1$-$C_6$-alkoxy-, trifluoromethoxy-, ($C_6$$H_5$)$_3$Si—, ($C_1$-$C_{12}$-alkyl)$_3$Si— or secondary amino-substituted phenyl, naphthyl, furyl or benzyl. R$_1$ may preferably be $C_1$-$C_8$-alkyl and more preferably $C_3$-$C_8$-alkyl, unsubstituted cyclopentyl or cyclohexyl, or cyclopentyl or cyclohexyl substituted by 1 to 3 $C_1$-$C_4$-alkyl or $C_1$-$C_4$-alkoxy, benzyl and phenyl which are unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl. Among the $C_3$-$C_8$-alkyl groups, preference is given to those which are branched in the α position.

When R$_1$ is a ferrocenyl radical, this radical may be unsubstituted or mono- or polysubstituted. This radical is preferably substituted by an ortho-directing group on the same cyclopentadiene ring in the ortho position to the bonded P*. This ortho-directing group may be vinyl, methyl, ethyl, a C-bonded chiral group which directs metals of metallating reagents into the ortho position, or a —CH$_2$—NR$_{11}$R$_{12}$ group.

This ortho-directing group is preferably a chiral group, for example of the formula —HC*R$_{14}$R$_{15}$ (* indicates the asymmetric atom) in which R$_{14}$ is $C_1$-$C_8$-alkyl, $C_5$-$C_8$-cycloalkyl (cyclohexyl), $C_6$-$C_{10}$-aryl (phenyl), $C_7$-$C_{12}$-aralkyl (benzyl) or $C_7$-$C_{12}$-alkaryl (methylbenzyl), R$_{15}$ is OR$_{16}$ or —NR$_{11}$R$_{12}$, R$_{16}$ is $C_1$-$C_8$-alkyl, $C_5$-$C_8$-cycloalkyl, phenyl or benzyl, and R$_{11}$ and R$_{12}$ are the same or different and are each $C_1$-$C_8$-alkyl, $C_5$-$C_8$-cycloalkyl, phenyl or benzyl or R$_{11}$ and R$_{12}$ together with the nitrogen atom form a five- to eight-membered ring. R$_{14}$ is preferably $C_1$-$C_4$-alkyl, for example methyl, ethyl, n-propyl and phenyl. R$_{16}$ is preferably $C_1$-$C_4$-alkyl, for example methyl, ethyl, n-propyl and n- or i-butyl. R$_{11}$ and R$_{12}$ are preferably identical radicals and are preferably each $C_1$-$C_4$-alkyl, for example methyl, ethyl, n-propyl, i-propyl and n- or i-butyl, and together tetramethylene, pentamethylene or 3-oxa-1,5-pentylene. Particularly preferred groups of the formula —HCR$_{14}$R$_{15}$ are 1-methoxyeth-1-yl, 1-dimethylaminoeth-1-yl and 1-(dimethylamino)-1-phenyl-methyl.

A preferred subgroup of inventive compounds is that of those of the formulae IIIa, VIIa, VIIIa, IXa and XXa

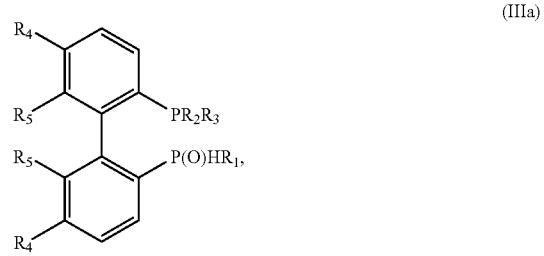

(IIIa)

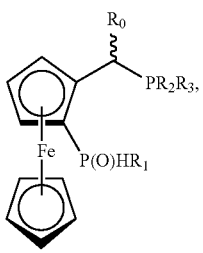
(VIIa)

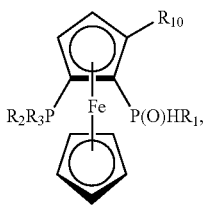
(VIIIa)

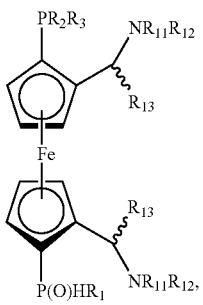
(IXa)

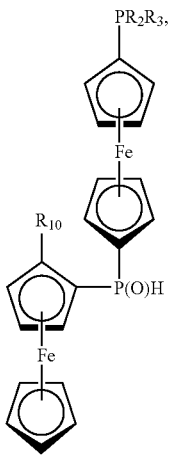

in which
the 3,3' and/or 4,4' positions in formula IIIa may be substituted by $C_1$-$C_4$-alkyl, $C_1$-$C_4$-alkoxy, trifluoromethyl or trimethylsilyl;
$R_1$ is $C_1$-$C_8$-alkyl, unsubstituted cyclopentyl or cyclohexyl or cyclopentyl or cyclohexyl substituted by 1 to 3 $C_1$-$C_4$-alkyl or $C_1$-$C_4$-alkoxy, or benzyl and phenyl which are unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl;
$R_2$ and $R_3$ are each independently a hydrocarbon radical which has 1 to 18 carbon atoms and is unsubstituted or substituted by $C_1$-$C_6$-alkyl, trifluoromethyl, $C_1$-$C_6$-alkoxy, trifluoromethoxy, $(C_1$-$C_4$-alkyl$)_2$amino, $(C_6H_5)_3$Si, $(C_1$-$C_{12}$-alkyl$)_3$Si, halogen, and/or O heteroatoms;
$R_4$ is hydrogen or independently as defined for $R_5$;
$R_5$ is $C_1$-$C_4$-alkyl, $C_1$-$C_4$-alkoxy, $C_1$-$C_4$-hydroxyalkyl, $C_2$-$C_4$-hydroxyalkoxy, $C_1$-$C_4$-alkoxy-$C_1$-$C_2$-alkyl, $C_1$-$C_4$-alkoxy-$C_1$-$C_2$-alkoxy, trifluoromethyl or trimethylsilyl, or $R_4$ and $R_5$ together are —CH=CH—CH=CH—, trimethylene, tetramethylene, —O—$CH_2$—O—, —O—$CF_2$—O—, —O—$CH_2$—$CH_2$—O—, —N(methyl)-$CH_2$—$CH_2$—O—;
the $R_5$ radicals together are $C_2$-$C_6$-alkylene, —O—($C_1$-$C_4$-alkylene)-O— or —O—$CF_2$—O—;
$R_9$ is $C_1$-$C_4$-alkyl, cyclopentyl, cyclohexyl, phenyl, methylphenyl, methylbenzyl or benzyl;
$R_{10}$ is —$CH_2$—$NR_{11}R_{12}$, —$CHR_9$—$NR_{11}R_{12}$, vinyl, methyl or ethyl; and
$R_{11}$ and $R_{12}$ are identical radicals, and $R_{11}$ and $R_{12}$ are each $C_1$-$C_4$-alkyl, cyclopentyl, cyclohexyl, phenyl, methylphenyl, methylbenzyl or benzyl, or $R_{11}$ and $R_{12}$ together are tetramethylene or 3-oxapentane-1,5-diyl; and
the $R_{13}$ are each $C_1$-$C_4$-alkyl, cyclopentyl, cyclohexyl, phenyl, methylphenyl, methylbenzyl or benzyl.

A very particularly preferred subgroup of inventive compounds is that of those of the formula VIIa.

The inventive compounds of the formula I are obtainable in a simple manner from halogenated precursors by first metallating the precursor, for example with lithium alkyl, then reacting the metallated compound with a dihalophosphine, a halomonoalkoxyphosphine or a halomono(dialkylamino) phosphine, and, in a last stage, forming the —P(=O)H$R_1$ group by hydrolysis. The reactions proceed with high yields and selectivities, and reaction products from the intermediate stages and the end stage may—if required—be purified by simple means, for example recrystallization and chromatographic purifications with achiral columns, for example on silica gels as the solid phase.

The invention further provides a process for preparing compounds of the formula I, which is characterized in that a compound of the formula X secondary phosphine-Q-Hal    (X)

in which secondary phosphine and Q are each as defined above and Hal is Cl, Br or I is reacted with a metallating reagent and thereafter with a halophosphine of the formula XI Hal-P$X_2R_1$    (XI), in which
$R_1$ is as defined in formula I including the preferences,
Hal is Cl, Br or I, and
$X_2$ is Cl, Br, I, $C_1$-$C_4$-alkoxy or $(C_1$-$C_4$-alkyl$)_2$amino, and
the compound of the formula XII formed secondary phosphine-Q-P$X_2R_1$    (XII)

is hydrolysed with water to give a compound of the formula I.
Compounds of the formula X are known or can be prepared by known or analogous processes. Ferrocenes of the formula XIII

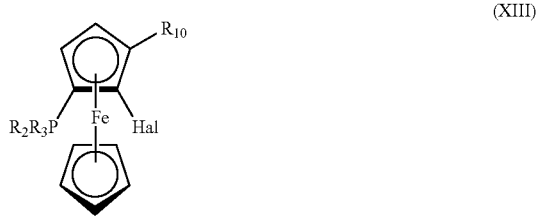
(XIII)

can be prepared analogously to the method described by M. Steurer et al. in Chem. Commun., 2005, 4929-4931, by halogenating, for example brominating, a ferrocene with the substituent $R_{10}$ in the ortho position, lithiating the halogenated ferrocene in the ortho position to the halogen by reacting with a lithium secondary amide (Li—NR$_2$), and then reacting the lithiated ferrocene with a halophosphine Hal-PR$_2$R$_3$.

Compounds in which R$_{10}$ is vinyl, ethyl or the —CH$_2$—NR$_{11}$R$_{12}$ group are prepared by modifying the R$_{10}$ group as a C-bonded chiral group which directs metals of metallating reagents into the ortho position after the halogenation, for example by eliminating the chiral auxiliary group to the vinyl group and subsequently hydrogenating it to the ethyl group. The —CH$_2$—NR$_{11}$R$_{12}$ group is obtained by substituting a CH$_2$-bonded chiral auxiliary group by HNR$_{11}$R$_{12}$.

The process conditions for organometallic syntheses are known and will not be described here in detail. Details can be taken from the examples.

The inventive compounds of the formula I are ligands for metal complexes selected from the group of the transition metals, which are excellent catalysts or catalyst precursors for asymmetric syntheses, for example the asymmetric hydrogenation of prochiral unsaturated organic compounds. When prochiral unsaturated organic compounds are used, a very high excess of optical isomers can be induced in the synthesis of organic compounds, and a high chemical conversion can be achieved in short reaction times. The achievable enantioselectivities and catalyst activities are excellent. Moreover, such ligands can also be used in other asymmetric addition or cyclization reactions.

The invention further provides metal complexes of transition metals of the transition groups of the Periodic Table of the Elements with a compound of the formula I as a ligand.

Among the transition metals, metals are more preferably selected from the group of Fe, Co, Ni, Cu, Ag, Au, Ru, Rh, Pd, Os, Ir. Very particularly preferred metals are Cu, Pd, Ru, Rh, Ir and Pt. Examples of organic syntheses are, as well as asymmetric hydrogenations of prochiral unsaturated organic compounds, amine couplings, enantioselective ring openings and hydrosilylations.

Particularly preferred metals are ruthenium, rhodium and iridium.

Depending on the oxidation number and coordination number of the metal atom, the metal complexes may contain further ligands and/or anions. The metal complexes may also be cationic metal complexes. Such analogous metal complexes and their preparation have been described many times in the literature.

The metal complexes may, for example, correspond to the general formulae XIV and XV

in which A$_1$ is a compound of the formula I,
L are identical or different monodentate, anionic or nonionic ligands, or two L are identical or different bidentate, anionic or nonionic ligands;
n is 2, 3 or 4 when L is a monodentate ligand, or n is 1 or 2 when L is a bidentate ligand;
z is 1, 2 or 3;
Me is a metal selected from the group Rh, Ir and Ru; where the metal has the oxidation states 0, 1, 2, 3 or 4;
E$^-$ is the anion of an oxygen acid or complex acid; and
the anionic ligands balance the charge of the 1, 2, 3 or 4 oxidation states of the metal.

For the compounds of the formula I, the above-described preferences and embodiments apply.

Monodentate nonionic ligands may, for example, be selected from the group of the olefins (for example ethylene, propylene), allyls (allyl, 2-methallyl), solvating solvents (nitriles, linear or cyclic ethers, optionally n-alkylated amides and lactams, amines, phosphines, alcohols, carboxylic esters, sulphonic esters), nitrogen monoxide and carbon monoxide.

Monodentate anionic ligands may, for example, be selected from the group of halide (F, Cl, Br, I), pseudohalide (cyanide, cyanate, isocyanate) and anions of carboxylic acids, sulphonic acids and phosphonic acids (carbonate, formate, acetate, propionate, methylsulphonate, trifluoromethylsulphonate, phenylsulphonate, tosylate).

Bidentate nonionic ligands may, for example, be selected from the group of the linear or cyclic diolefins (for example hexadiene, cyclooctadiene, norbornadiene), dinitriles (malononitrile), optionally N-alkylated carboxamides, diamines, diphosphines, diols, acetonylacetonates, dicarboxylic esters and disulphonic esters.

Bidentate anionic ligands may, for example, be selected from the group of the anions of dicarboxylic acids, disulphonic acids and diphosphonic acids (for example of oxalic acid, malonic acid, succinic acid, maleic acid, methylenedisulphonic acid and methylenediphosphonic acid).

Preferred metal complexes are also those in which E is —Cl$^-$, —Br$^-$, —I$^-$, ClO$_4^-$, CF$_3$SO$_3^-$, —CH$_3$SO$_3^-$, HSO$_4^-$, (CF$_3$SO$_2$)$_2$N$^-$, (CF$_3$SO$_2$)$_3$C$^-$, tetraarylborates, for example B(phenyl)$_4^-$, B[bis(3,5-trifluoromethyl)phenyl]$_4^-$, B[bis(3,5-dimethyl)phenyl]$_4^-$, B(C$_6$F$_5$)$_4^-$ and B(4-methylphenyl)$_4^-$, BF$_4^-$, PF$_6^-$, SbCl$_6^-$, AsF$_6^-$ or SbF$_6^-$.

Especially preferred metal complexes which are suitable particularly for hydrogenations correspond to the formulae XVI and XVII

in which
A$^1$ is a compound of the formula I;
Me$_2$ is rhodium or iridium;
Y is two olefins or one diene;
Z is Cl, Br or I; and
E$_1^-$ is the anion of an oxygen acid or complex acid.

For the compounds of the formula I, the above-described embodiments and preferences apply.

When Y is defined as olefin, it may be C$_2$-C$_{12}$-olefins, preferably C$_2$-C$_6$-olefins and more preferably C$_2$-C$_4$-olefins. Examples are propene, but-1-ene and particularly ethylene. The diene may contain 5 to 12 and preferably 5 to 8 carbon atoms, and may be open-chain, cyclic or polycyclic dienes. The two olefin groups of the diene are preferably bonded by one or two CH$_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y is preferably two ethylene, or 1,5-hexadiene, 1,5-cyclooctadiene or norbornadiene.

In formula XVI, Z is preferably Cl or Br. Examples of E$_1$ are BF$_4^-$, ClO$_4^-$, CF$_3$SO$_3^-$, CH$_3$SO$_3^-$, HSO$_4^-$, B(phenyl)$_4^-$, B[bis(3,5-trifluoromethyl)phenyl]$_4^-$, PF$_6^-$, SbCl$_6^-$, AsF$_6^-$ or SbF$_6^-$.

The inventive metal complexes are prepared by methods known in the literature (see also U.S. Pat. No. 5,371,256, U.S. Pat. No. 5,446,844, U.S. Pat. No. 5,583,241 and E. Jacobsen, A. Pfaltz, H. Yamamoto (Eds.), Comprehensive Asymmetric Catalysis I to III, Springer Verlag, Berlin, 1999, and literature cited therein).

The inventive metal complexes are homogeneous catalysts or catalyst precursors which are activable under the reaction conditions and can be used for asymmetric addition reactions to prochiral unsaturated organic compounds; see E. Jacobsen, A. Pfaltz, H. Yamamoto (Eds.), Comprehensive Asymmetric Catalysis I to III, Springer Verlag, Berlin, 1999, and B. Cornils et al., in Applied Homogeneous Catalysis with Organometallic Compounds, Volume 1, Second Edition, Wiley VCH-Verlag, (2002). Further applications are, for example, the amination of aromatics or heteroaromatics which contain leaving groups, for example halide or sulphonate, with primary or secondary amines with palladium complexes, or the preferably Rh— catalysed enantioselective ring-opening reaction of oxabicyclic alkanes (M. Lautens et al. in Acc. Chem. Res. Volume 36 (203), pages 48-58).

The metal complexes may, for example, be used for the asymmetric hydrogenation (addition of hydrogen) of prochiral compounds with carbon/carbon or carbon/heteroatom double bonds. Such hydrogenations with soluble homogeneous metal complexes are described, for example, in Pure and Appl. Chem., Vol. 68, No. 1, pages 131-138 (1996). Preferred unsaturated compounds to be hydrogenated contain the C=C, C=N and/or C=O groups. For the hydrogenation, preference is given in accordance with the invention to using metal complexes of ruthenium, rhodium and iridium.

The invention further provides for the use of the inventive metal complexes as homogeneous catalysts for preparing chiral organic compounds by asymmetric addition of hydrogen to a carbon or carbon-heteroatom double bond in prochiral organic compounds.

A further aspect of the invention is a process for preparing chiral organic compounds by asymmetric addition of hydrogen to a carbon or carbon-heteroatom double bond in prochiral organic compounds in the presence of a catalyst, which is characterized in that the addition is performed in the presence of catalytic amounts of at least one inventive metal complex.

Preferred prochiral unsaturated compounds to be hydrogenated may contain one or more identical or different C=C, C=N and/or C=O groups in open-chain or cyclic organic compounds, where the C=C, C=N and/or C=O groups may be part of a ring system or be exocyclic groups. The prochiral unsaturated compounds may be alkenes, cycloalkenes, heterocycloalkenes, and also open-chain or cyclic ketones. α,β-diketones, α- or β-ketocarboxylic acids and their α,β-ketoacetals or -ketals, esters and amides, ketimines and kethydrazones. Alkenes, cycloalkenes, heterocyclo-alkenes also include enamides.

The process according to the invention can be performed at low or elevated temperatures, for example temperatures of −20 to 150° C., preferably of −10 to 100° C., and more preferably of 10 to 80° C. The optical yields are generally better at relatively low temperature than at relatively high temperatures.

The process according to the invention can be performed at standard pressure or elevated pressure. The pressure may, for example, be $10^5$ to $2 \times 10^7$ Pa (pascal). Hydrogenations may be performed at standard pressure or at elevated pressure.

Catalysts are used preferably in amounts of 0.00001 to 10 mol %, more preferably 0.00001 to 5 mol % and especially preferably 0.00001 to 2 mol %, based on the compound to be hydrogenated.

The preparation of the ligands and catalysts and the hydrogenation can be performed without or in the presence of an inert solvent, in which case one solvent or mixtures of solvents may be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halohydrocarbons (methylene chloride, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl acetate or methyl acetate, valerolactone), N-substituted lactams (N-methylpyrrolidone), carboxamides (dimethylacetamide, dimethylformamide), acyclic ureas (dimethylimidazoline), and sulphoxides and sulphones (dimethyl sulphoxide, dimethyl sulphone, tetramethylene sulphoxide, tetramethylene sulphone) and optionally fluorinated alcohols (methanol, ethanol, propanol, butanol, ethylene glycol monomethyl ether, ethylene glycol monoethyl ether, diethylene glycol monomethyl ether, 1,1,1-trifluoroethanol) and water. Suitable solvents are also low molecular weight carboxylic acids, for example acetic acid.

The reactions can be performed in the presence of cocatalysts, for example quaternary ammonium halides (tetrabutylammonium chloride, bromide or iodide) or protic acids, for example mineral acids such as HCl or strong organic acids such as trifluoroacetic acid, or mixtures of such halides and acids (see, for example, U.S. Pat. No. 5,371,256, U.S. Pat. No. 5,446,844 and U.S. Pat. No. 5,583,241 and EP-A-0 691 949). The presence of fluorinated alcohols, for example 1,1,1-trifluoroethanol, can also promote the catalytic reaction. The addition of bases, for example tertiary amines or phosphines, alkali metal hydroxides, secondary amides, alkoxides, carbonates and hydrogencarbonates may also be advantageous. The selection of a cocatalyst is guided mainly by the metal in the metal complex and the substrate. In the hydrogenation of prochiral arylketimines, the use of iridium complexes in combination with tetra-$C_1$-$C_4$-alkylammonium iodides and mineral acids, preferably HI, has been found to be useful.

The metal complexes used as catalysts may be added as separately prepared isolated compounds, or else formed in situ before the reaction and then mixed with the substrate to be hydrogenated. It may be advantageous to additionally add ligands in the reaction using isolated metal complexes, or to use an excess of the ligands in the in situ preparation. The excess may, for example, be 1 to 6 mol and preferably 1 to 2 mol, based on the metal compound used for the preparation.

The process according to the invention is generally performed in such a way that the catalyst is initially charged and then the substrate, optionally reaction assistant and the compound to be added on are added, and then the reaction is started. Gaseous compounds to be added on, for example hydrogen, are preferably injected under pressure. The process can be performed continuously or batchwise in various reactor types.

The chiral organic compounds preparable in accordance with the invention are active substances or intermediates for preparing such substances, especially in the sector of the preparation of aromas and flavourings, pharmaceuticals and agrochemicals.

The examples which follow illustrate the invention. All reactions are performed with the exclusion of air under argon and with degassed solvents.

A) PREPARATION OF LIGANDS

Example A1

Preparation of Ligand L1

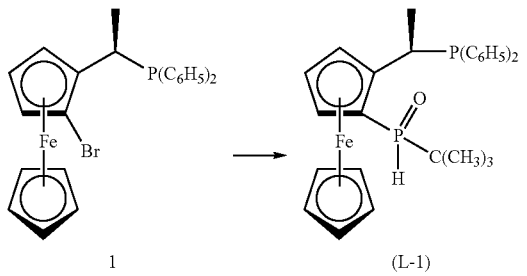

The synthesis of compound 1 is described in the literature: P. Barbaro et al., Tetrahedron Letter 44 (2003)-8279-8283.

1.93 ml (3.1 mmol) of 1.6 molar solution of n-butyl-Li (n-Bu—Li) in hexane are slowly added dropwise at −25° C. to a solution of 1.42 g (3 mmol) of compound 1 in 10 ml of diethyl ether (DEE). After stirring at −25° C. for 30 minutes, the reaction mixture is cooled to −78° C., and a solution of 3.3 mmol of dichloro-t-butylphosphine in 20 ml of DEE is added slowly. After stirring at −78° C. for 10 minutes, the cooling bath is removed and the mixture is allowed to rise to room temperature overnight. The reaction mixture is subsequently admixed with 30 ml of degassed water and extracted with DEE. The organic phases are collected, dried over sodium sulphate and concentrated to dryness under reduced pressure on a rotary evaporator. The crude product is purified by chromatography (silica gel 60, eluent=ethyl acetate [EA]). The ligand L1 is obtained as a pure diastereomer and as a yellow solid in a yield of 81%. $^{31}$P NMR (acetone$_{d6}$, 161.97 MHz): δ 32.6 (s), 4.8 (s). $^1$H NMR (C$_6$D$_6$, 300 MHz) characteristic signals: 7.51-7.01 (m, 10H), 6.20 (d, $^1J_{PH}$=460 Hz, PH), 4.48 (s, 2H), 4.37 (s, 5H), 4.24 (s, 1H), 3.88-3.74 (m, 1H), 1.51 (m, 3H), 1.13 (d, 9H).

Example A2

Preparation of Ligand L2

The procedure is analogous to Example A1, except that dichlorophenylphosphine is used in place of dichloro-t-butylphosphine. The ligand L2 is obtained as a pure diastereomer and as a yellow solid in a yield of 61%. $^{31}$P NMR (CDCl$_3$, 161.97 MHz): δ 14.6 (s), 6.4 (s). $^1$H NMR (C$_6$D$_6$, 300 MHz) characteristic signals: 7.74-6.93 (m, 15H), 6.37 (d, $^1J_{PH}$=495 Hz, PH), 4.44 (s, 1H), 4.30 (s, 1H), 4.27 (s, 5H), 4.08-3.98 (m, 1H), 3.53 (s, 1H), 1.53 (m, 3H).

Example A3

Preparation of Ligand L3

The synthesis of compound 2 is described in WO 96/16971.

a) Preparation of Compound 3

12.1 ml (15.7 mmol) of a 1.3 molar secondary butyl-Li (s-BuLi) solution in cyclohexane are slowly added dropwise with ice cooling and stirring to 5.0 g (13 mmol) of compound 2 (S,S' configuration) in 30 ml of tert-butyl methyl ether (TBME) at such a rate that the temperature of the reaction mixture does not exceed 2° C. The reaction mixture is stirred further at 0° C. over 1.5 hours, then 5.3 g (15.7 mmol) of bis(3,5-dimethyl-4-methoxyphenyl)phosphine chloride are added dropwise to the red-orange suspension within 15 minutes. After further stirring at 0° C. for one hour, the cooling is removed. The reaction mixture is allowed to warm slowly to room temperature and stirred for another 1 hour, and then admixed with 10 ml of water. The mixture is extracted first with EA and then with TBME. The organic phases are combined and dried over sodium sulphate, and the solvent is distilled off completely under reduced pressure in a rotary evaporator. The crude product is purified by chromatography (silica gel 60, eluent=2:1 heptane/EA with 2% triethylamine). The pure compound 3 is obtained as a yellow solid with a yield of 67%. $^{31}$P NMR (C$_6$D$_6$, 121 MHz): δ −23.5 (s). $^1$H NMR (C$_6$D$_6$, 300 MHz) characteristic signals: δ 7.60 (d, 2H), 7.14 (d, 2H), 4.37 (m, 1H), 4.24 (m, 1H), 4.19 (m, 1H), 4.14 (m, 1H), 4.02 (m, 2H), 3.86 (m, 2H), 3.39 (s, 3H), 3.30 (s, 1H), 2.78 (q, 1H), 2.17 (s, 6H), 2.12 (s, 6H), 2.02 (s, 6H), 1.94 (s, 6H), 1.20 (m, 6H).

b) Preparation of Ligand L3

2.4 ml of a 1.3 molar solution of s-BuLi in cyclohexane are added dropwise at −20° C. with stirring to a solution of 1.6 g (2.5 mmol) of compound 3 in 20 ml of TBME, and the reaction mixture is subsequently stirred further at this temperature for another 1.5 hours. The red-orange solution is then cooled to −78° C., and a solution of 0.8 g (5 mmol) of t-butyldichlorophosphine is slowly added dropwise. The mixture is stirred at −78° C. for another one hour, then the cooling bath is removed and the mixture is allowed to warm to room temperature overnight. The reaction mixture is admixed with 10 ml of water, neutralized with a saturated NaHCO$_3$ solution and extracted with TBME. The organic phases are collected and dried over sodium sulphate, and the solvent is distilled off completely under reduced pressure on a rotary evaporator. The solid orange crude product (1.9 g) is purified by chromatography (silica gel 60, eluent=1:1 heptane/EA with 1% triethylamine). The pure compound L3 is obtained as a yellow solid with a yield of 66%. $^{31}$P NMR (C$_6$D$_6$, 121 MHz): δ +35.6 (s), −24.8 (s). $^1$H NMR (C$_6$D$_6$, 300 MHz) characteristic signals: δ 7.67 (d, 2H), 7.21 (d, 2H), 7.12 (d, $^1J_{PH}$=465 Hz, 1H), 5.21 (m, 1H), 4.79 (m, 1H), 4.39 (m, 1H), 4.34 (m, 1H), 4.30 (m, 1H), 4.31-4.09 (m, 2H), 3.63 (m, 1H), 3.41 (s, 3H), 3.32 (s, 3H), 2.22 (s, 6H), 2.12 (s, 6H), 2.01 (s, 6H), 1.94 (s, 6H), 1.30 (d, 3H), 1.21 (d, 3H), 0.99 (d, 9H).

Example A4

Preparation of Ligands L4 and L5

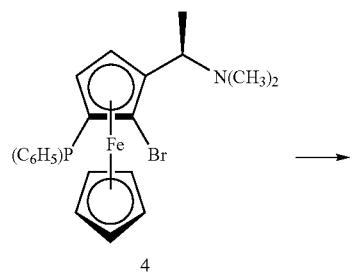

4

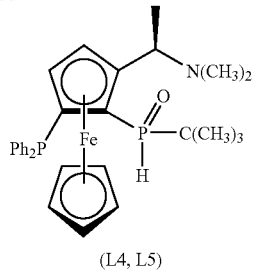

(L4, L5)

a) Preparation of Compound 4

12.9 ml (75.9 mmol, 3.0 equivalents) of 2,2,6,6-tetramethylpiperidine are dissolved in 100 ml of absolute tetrahydrofuran (THF) and cooled to 0° C. 45.8 ml (73.4 mmol, 2.9 equivalents) of n-Bu—Li solution (1.6 m in hexane) are added dropwise. Subsequently, the mixture is stirred at 0° C. for one hour (solution A).

8.50 g (25.3 mmol, 1.0 equivalent) of compound 1 are dissolved in 70 ml of absolute THF and cooled to −70° C. (solution B).

Solution A is added dropwise to solution B with stirring over 30 minutes, in the course of which it is ensured that the temperature does not exceed −30° C. The mixture is then stirred further over 1.5 hours, in the course of which the temperature is kept at −35° C. Thereafter, the reaction mixture is cooled to −78° C., and 6.1 ml (32.9 mmol, 1.3 equivalents) of diphenylphosphine chloride are added. The temperature is allowed to rise slowly to −25° C. with stirring within 1.5 hours. The reaction mixture is then admixed with 100 ml of water. The mixture is extracted with TBME. The combined organic phases are dried over sodium sulphate and freed of the solvent on a rotary evaporator. The resulting brown oil is purified chromatographically (silica gel 60, eluent=acetone). The chromatographed product is obtained in virtually quantitative yield. Recrystallization in methanol gives rise to the compound 4 as a yellow-orange solid in a yield of 73%. $^{31}$P NMR (C$_6$D$_6$, 121 MHz): δ −18.2 (s). $^1$H NMR (C$_6$D$_6$, 300 MHz) characteristic signals: δ 7.66-6.90 (10 aromatic H), 4.03 (s, 5H), 3.96 (m, 1H), 3.90 (q, 1H), 2.18 (s, 6H), 1.31 (d, 3H).

b) Preparation of the Diastereomeric Ligands L4 and L5

1.5 ml of a 1.6 molar solution of n-Bu—Li in hexane are added dropwise at 0° C. with stirring to a solution of 1.0 g (1.9 mmol) of compound 4 in 20 ml of TBME, and the reaction mixture is subsequently stirred further at this temperature for another 2 hours. The red-orange solution is then cooled to −78° C., and a solution of 0.6 g (3.8 mmol) of t-butyldichlorophosphine is slowly added dropwise. The mixture is stirred at −78° C. for another one hour. The cooling bath is then removed and the temperature is allowed to rise to room temperature overnight. The reaction mixture is admixed with 10 ml of water, neutralized with unsaturated NaHCO$_3$ solution and extracted with TBME. The organic phases are collected and dried over sodium sulphate, and the solvent is distilled off completely under reduced pressure on a rotary evaporator. The resulting solid orange crude product (1.2 g) contains two diastereomers. These are separated by chromatography (silica gel 60, eluent=2:1 heptane/EA with 1% triethylamine). The first fraction affords 266 mg of the first diastereoisomer ligand L4 (yellow solid, 27% yield), and the second, larger fraction 560 mg of the second diastereomer L5 (yellow solid, 55% yield).

Ligand L4: $^{31}$P NMR (CD$_3$OD, 121 MHz): δ +47.8, −22.2. $^1$H NMR (CD$_3$OD, 300 MHz) characteristic signals: 7.69-

7.12 (various signals, 10H), 7.0 (d, $^1J_{PH}$=470 Hz, 1H), 4.78 (m, 1H), 4.42 (m, 1H), 4.07 (s, 5H), 2.09 (s, 6H), 1.33 (d, 3H), 1.05 (d, 9H).

Ligand L5: $^{31}$P NMR (CD$_3$OD, 121 MHz): δ +48.5 (d), −24.9 (d). $^1$H NMR (CD$_3$OD, 300 MHz) characteristic signals: 7.65-7.12 (various signals, 10H), 7.73 (d of d, $^1J_{PH}$=472 Hz, 1H), 4.83 (m, 1H), 4.30 (m, 1H), 4.05 (s, 5H), 2.12 (s, 6H), 1.29 (d, 3H), 1.03 (d, 9H).

Example A5

Preparation of Ligand L6

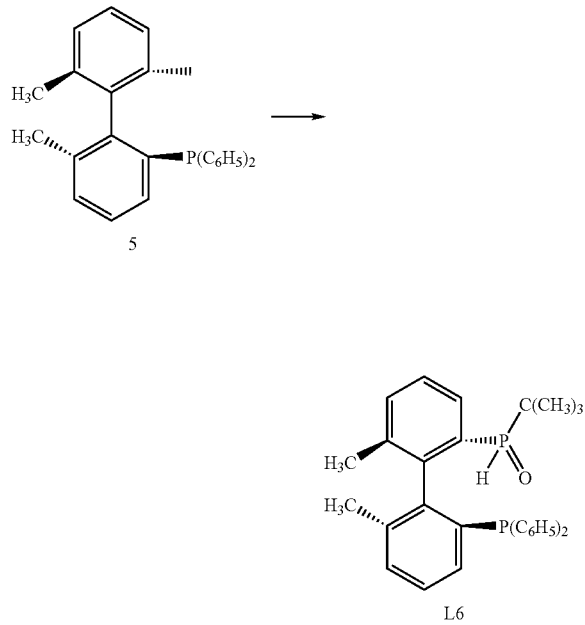

a) Preparation of Compound 5

The preparation of compound 5 is described by M. Cereghetti et al. in Tetrahedron Letter 37 (1996) 5347-5350.

b) Preparation of Ligand L6

0.75 ml (1.2 mmol) of n-Bu—Li (1.6 M in hexane) is added dropwise at −78° C. with stirring to a solution of 500 mg (1 mmol) of compound 5 in 15 ml of TBME. After stirring at −78° C. for 1 hour, 320 mg (2 mmol) of t-butyldichlorophosphine are added. After 2 hours, the cooling is removed and the temperature is allowed to rise to room temperature overnight. The reaction mixture is admixed with 10 ml of water and extracted with TBME. The organic phases are collected, washed with aqueous NaHCO$_3$ solution and then with NaCl solution, and dried over sodium sulphate, and the solvent is distilled off completely on a rotary evaporator. The crude product contains the desired product as a mixture of 2 diasteromers in a ratio of about 5:2 (crude yield 77%). These can be separated by column chromatography (silica gel 60, eluent=first 1:2 EA/heptane, then 1:1 and finally only EA). The diastereomer obtained in a larger amount is referred to as ligand L6, which is eluted before the diasteromer present in a smaller amount (both are white solids). Ligand L6: $^{31}$P NMR (C$_6$D$_6$, 121 MHz): δ +36.5, −16.0. $^1$H NMR (C$_6$D$_6$, 300 MHz) characteristic signals: δ 8.02-6.88 (16 arom. H), 6.98 (d, $^1J_{PH}$=461 Hz, 1H), 1.81 (s, 3H), 1.36 (s, 3H), 0.96 (s, 9H).

Example A6

Preparation of Ligand L7 a) Preparation of Compound 6

5.21 g of compound 1 (15.5 mmol) in 30 ml of acetic anhydride are heated to 135° C. with stirring over 4 hours. After cooling, the mixture is extracted with water/toluene. The organic phases are collected and dried over sodium sulphate, and the solvents are distilled off completely on a rotary evaporator under reduced pressure (20 torr). The crude product is then purified by chromatography (silica gel 60, eluent=heptane). Compound 6 is obtained as a red-brown oil in a yield of 80%. $^1$H NMR (C$_6$D$_6$, 300 MHz) characteristic signals: δ 6.89 (m, 1H), 5.38 (m, 1H), 5.08 (m, 1H), 4.28 (m, 1H), 4.16 (m, 1H), 3.94 (s, 5H), 3.80 (m, 1H).

b) Preparation of Compound 7

A solution of 7.1 g (24.4 mmol) of compound 6 in 35 ml of THF is stirred intensively in the presence of 0.7 g of catalyst (5% Rh/C, Engelhard) in a hydrogen atmosphere (standard pressure) until no further hydrogen is consumed. The reaction mixture is then placed under argon and the catalyst is filtered off. After washing with a little THF, the filtrate is free from the solvent completely on a rotary evaporator. Compound 8 is obtained in quantitative yield as an orange-brown oil. $^1$H NMR (C$_6$D$_6$, 300 MHz) characteristic signals: δ 4.24 (m, 1H), 3.96 (s, 5H), 3.77 (m, 1H), 3.71 (m, 1H), 2.42-2.23 (m, 2H), 1.05 (t, 3H).

c) Preparation of Compound 8

1.74 ml (10.2 mmol, 3.0 equivalents) of 2,2,6,6-tetramethylpiperidine are dissolved in 20 ml of absolute THF and cooled to 0° C. 6.2 ml (9.9 mmol, 2.9 equivalents) of n-Bu—Li solution (1.6 m in hexane) are added dropwise. Subsequently, the mixture is stirred at 0° C. for one hour (solution A).

1.0 g (3.41 mmol, 1.0 equivalent) of compound 7 are dissolved in 10 ml of absolute THF and cooled to −70° C. (solution B).

Solution A is added dropwise to solution B over 30 minutes, in the course of which it is ensured that the temperature does not exceed −30° C. The mixture is then stirred over 4 hours, in the course of which the temperature is kept between −40° C. and −30° C. The reaction mixture is cooled to −78° C., and 0.82 ml (4.44 mmol, 1.3 equivalents) of diphenylphosphine chloride is added. The temperature is allowed to rise slowly to −25° C. with stirring within 1.5 hours. The reaction mixture is then admixed with 20 ml of water. After adding a little saturated ammonium chloride solution, the mixture is extracted with DEE and methylene chloride. The combined organic phases are dried over sodium sulphate and freed of the solvent on a rotary evaporator. The resulting brown oil is purified chromatographically (silica gel 60, eluent=first 20:1 heptane-EA, then 10:1 heptane-EA). Compound 8 is obtained as a brown solid with a yield of 62%. $^{31}$P NMR ($C_6D_6$, 121 MHz): δ −18.2 (s). $^1$H NMR ($C_6D_6$, 300 MHz) characteristic signals: δ 7.62 (m, 2H), 7.38 (m, 2H), 7.1-6.9 (m, 6H), 3.99 (s, 5H), 3.94 (m, 1H), 3.59 (m, 1H), 2.47-2.26 (m, 2H), 1.07 (t, 3H).

d) Preparation of Ligand L7

0.31 ml (0.50 mmol) of a 1.6 molar solution of n-Bu—Li in hexane are slowly added dropwise at −30° C. to a solution of 200 mg (0.419 mmol) of compound 8 in 10 ml of TBME. After stirring at −30° C. for 1 hour, the reaction mixture is cooled to −78° C., and 0.11 ml (0.84 mmol) of dichlorophenylphosphine is added slowly. After stirring at −78° C. for 20 minutes, the cooling bath is removed and the mixture is allowed to warm to room temperature overnight. The reaction mixture is subsequently admixed with 10 ml of degassed water, the pH is adjusted to 7-8 with saturated aqueous $NaHCO_3$ solution, and then the mixture is extracted with EA. The organic phases are collected, dried over sodium sulphate and concentrated to dryness under reduced pressure on a rotary evaporator. The crude product is purified by chromatography (silica gel 60, eluent=increasingly polar:first 1:3 EA/heptane, then 1:1 and finally pure EA). The ligand L7 is obtained as a pure diastereomer and as a yellow solid in a yield of 45%. $^{31}$P NMR ($C_6D_6$, 121 MHz): δ +13.4 (d), −24.0 (d). $^1$H NMR ($C_6D_6$, 300 MHz) characteristic signals: δ 8.82 and 7.73 (d of d, $^1J_{PH}$=489 Hz, 1H), 7.60-6.80 (15 aromatic H), 4.31 (s, 5H), 4.22 (m, 1H), 3.94 (m, 1H), 2.84 (m, 2H), 0.97 (t, 3H).

Example A7 and A8

Preparation of Ligands L8 and L9

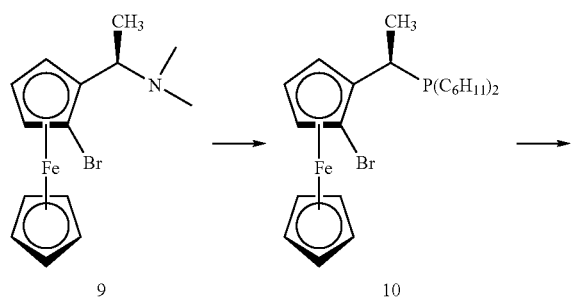

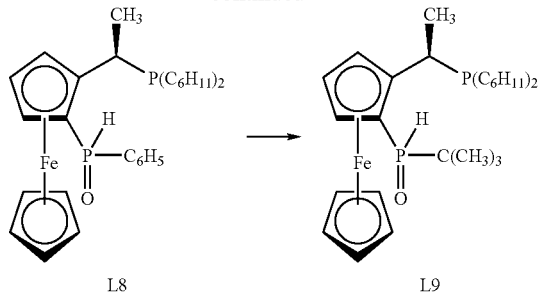

Compound 9 (1-[(dimethylamino)eth-1-yl]-2-bromoferrocene) is prepared as described in the literature: J. W. Han et al., Helv. Chim. Acta, 85 (2002) 3848-3854.

a) Preparation of Compound 10

10 g (29.8 mmol) of compound 9 and 7.22 ml (35.7 mmol) of dicyclohexylphosphine are stirred in 40 ml of acetic acid at 85° C. over 15 hours and then at 100° C. for 5 hours. After cooling, the red-brown solution is extracted with water and toluene, and then with saturated aqueous sodium chloride solution and toluene. The organic phase is dried over sodium sulphate, and the solvent is distilled off on a rotary evaporator. After chromatographic purification using a short column (150 g of silica gel 60; eluent=ethyl acetate EA), the desired red-brown product 10 is obtained in a yield of 95%. $^{31}$P NMR ($C_6D_6$, 121 MHz): δ +22.5 (s). $^1$H NMR ($C_6D_6$, 300 MHz): δ 4.29 (m, 1H), 4.02 (s, 5H), 3.89 (m, 1H), 3.76 (m, 1H), 3.105 (q, 1H), 1.57 (d of d, 3H), 2.0-1.0 (m, 22H).

b) Preparation of Compound L8:

4.3 ml (6.77 mmol) of n-BuLi (1.6 M in hexane) are added dropwise at 0° C. to a suspension of 3.01 g (6.15 mmol) of compound 10 in 30 ml of diethyl ether. The resulting red-brown solution is stirred further at 0° C. for 30 min before it is cooled to −70° C. 0.92 ml (6.7 mmol) of P,P-dichlorophenylphosphine are then added. The cooling is removed and the resulting light brown-orange suspension is stirred at room temperature for 2 hours. The reaction mixture is then hydrolysed with 20 ml of water and then extracted with water and methylene chloride. The organic phase is dried over sodium sulphate and the solvent is distilled off on a rotary evaporator. The crude product can be purified by chromatography (silica gel 60; eluent=1:1 EA/heptane in the presence of 0.4% triethylamine). The desired product L8 is obtained as a firm light brown solid (yield 40%). $^{31}$P NMR ($C_6D_6$, 121 MHz): δ +14.99 (d, $J_{PP}$=30 Hz), +13.95 (d, $J_{PP}$=30 Hz). $^1$H NMR ($C_6D_6$, 300 MHz): δ 9.45 and 7.82 (two d, 1H), 7.75-7.68 (m, 2H), 7.15-7.02 (m, 3H), 4.29 (s, 5H), 4.14 (s, 1H), 3.93 (q, 1H), 3.87 (m, 1H), 3.59 (m, 1H), 1.52 (d of d, 3H), 2.0-1.0 (m, 22H).

c) Preparation of Compound L9:

4.3 ml (6.77 mmol) of n-BuLi (1.6 M in hexane) are added dropwise at 0° C. to a suspension of 3.0 g (6.13 mmol) of compound 10 in 15 ml of diethyl ether. The resulting red-brown solution is stirred further at 0° C. for 30 min before it is cooled to −70° C. A solution of 1.07 g (6.7 mmol) of P,P-dichloro-tert-butylphosphine in 5 ml of diethyl ether (DEE) is then added. The cooling is removed and the resulting thick orange-red suspension is stirred at room temperature for 2 hours. The reaction mixture is then hydrolysed with 20 ml of water, and subsequently extracted with water, saturated aqueous sodium chloride solution and methylene chloride. The organic phase is dried with sodium sulphate, and the solvent is distilled off on a rotary evaporator. The crude product can be purified by chromatography (silica gel 60; eluent=EA with 0.4% triethylamine). The desired product L9 is obtained as a solid yellow-orange-brown solid (yield 64%). $^{31}$P NMR (C$_6$D$_6$, 121 MHz): δ +34.99 (d, J$_{PP}$=28 Hz), +12.81 (d, J$_{PP}$=28 Hz). $^1$H NMR (C$_6$D$_6$, 300 MHz) characteristic signals: δ 8.34 and 6.82 (two d, 1H), 4.40 (s, 5H), 4.28 (m, 1H), 4.08 (m, 1H), 4.03 (m, 1H), 3.48 (q of d, 1H), 1.47 (d of d, 3H), 1.24 and 1.18 (s, 9H), 2.0-1.0 (m, 22H).

Example A9

Preparation of Ligand L10

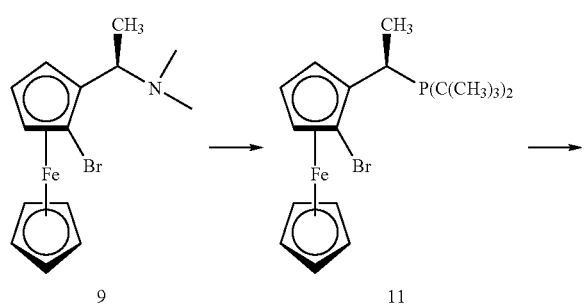

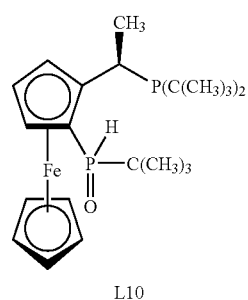

L10 a) Preparation of Compound 11

5 g (14.9 mmol) of compound 9 in 23.8 g of a 10% solution of di-tert-butylphosphine in acetic acid are stirred at 105° C. over 7.5 hours. After cooling, the red-brown solution is extracted with water and toluene and then with saturated aqueous sodium chloride solution and methylene chloride. The organic phases are dried over sodium sulphate, and the solvent is distilled off on a rotary evaporator. After chromatographic purification using a short column (150 g of silica gel 60; eluent=EA with 1% triethylamine), the desired red-brown product 11 is obtained in a yield of 70%. $^{31}$P NMR (C$_6$D$_6$, 121 MHz): δ +47.23 (s). $^1$H NMR (C$_6$D$_6$, 300 MHz) characteristic signals: 4.31 (m, 1H), 3.99 (s, 5H), 3.83 (m, 1H), 3.70 (m, 1H), 3.19 (q, 1H), 1.73 (d of d, 3H), 1.34 (d, 9H), 1.15 (d, 9H).

b) Preparation of Compound L10:

3.2 ml (5.11 mmol) of n-BuLi (1.6 M in hexane) are added dropwise at 0° C. to a solution of 2.03 g (4.64 mmol) of compound 11 in 20 ml of diethyl ether (DEE). The resulting red-orange suspension is stirred further at 0° C. for 1.5 hours before it is cooled to −70° C. A solution of 0.81 g (6.7 mmol) of P,P-dichloro-tert-butylphosphine, in 5 ml of DEE is then added. The cooling is removed and the resulting orange suspension is stirred at room temperature for 2 hours. The reaction mixture is then hydrolysed by adding 20 ml of water, and subsequently extracted with 0.05N NaOH and methylene chloride. The organic phase is dried over sodium sulphate and the solvent is distilled off on a rotary evaporator. The crude product can be purified by chromatography (silica gel 60; eluent=EA with 0.4% triethylamine). The desired product L10 is obtained as a red-orange, almost solid oil (yield 85%). $^{31}$P NMR (C$_6$D$_6$, 121 MHz): δ +44.83 (d, J$_{PP}$=39 Hz), +35.01 (d, J$_{PP}$=39 Hz). $^1$H NMR (C$_6$D$_6$, 300 MHz) characteristic signals: δ 8.51 and 6.96 (two d, 1H), 4.35 (s, 5H), 4.19 (m, 1H), 4.14 (m, 1H), 3.80 (q, 1H), 3.99 (m, 1H), 1.75 (d of d, 3H), 1.36 and 1.32 (two s, 9H), 1.22 and 1.16 (two s, 9H), 1.12 and 1.09 (two s, 9H).

Example A10

Preparation of Ligand L11

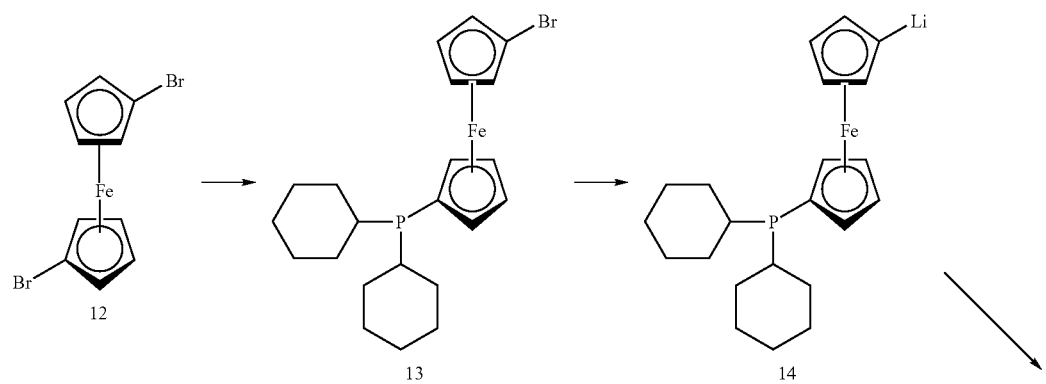

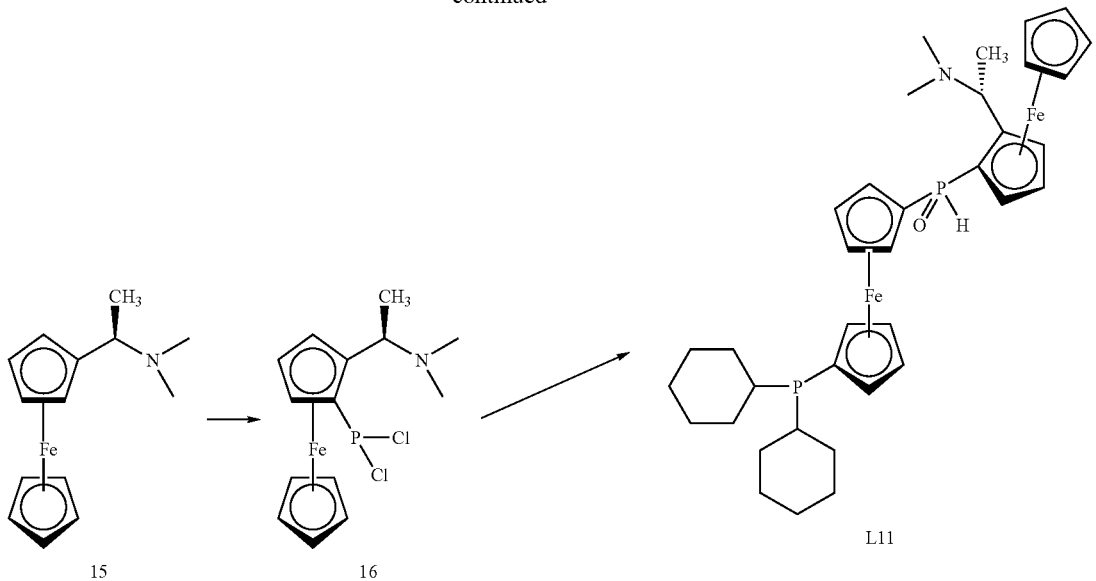

a) Preparation of 1-dicyclohexylphosphino-1'-bromoferrocene of the Formula 13:

120 ml (0.3 mol) of n-BuLi (2.5 M in hexane) are added dropwise at a temperature of <−30° C. to a solution of 103 g (0.3 mol) of 1,1'-dibromoferrocene in 300 ml of THF. The mixture is stirred further at this temperature for 1.5 hours. The mixture is then cooled to −50° C., and 66.2 ml (0.3 mol) of dicyclohexylphosphine chloride are slowly added dropwise at such a rate that the temperature does not rise above −45° C. After stirring for a further 10 minutes, the temperature is allowed to rise to room temperature and the mixture is stirred for another one hour. After adding 150 ml of water, the reaction mixture is extracted by shaking with hexane. The organic phases are dried over sodium sulphate, and the solvent is distilled off under reduced pressure on a rotary evaporator. The residue is crystallized in ethanol. The product 13 is obtained with a yield of 84% (yellow solid). $^1$H NMR (300 MHz, $C_6D_6$): δ 1.20~2.11 (m, 22H), 3.97 (m, 2H), 4.23 (m, 2H), 4.26 (m, 2H), 4.41 (m, 2H). $^{31}$P NMR (121.5 MHz, $C_6D_6$): δ −8.3 (s).

b) Preparation of Compound 16 (Reaction Solution 1):

4.0 ml (5.2 mmol) of s-BuLi (1.3 M in cyclohexanone) are added dropwise at −78° C. with stirring to a solution of 1.29 g (5 mmol) of compound 15 in 5 ml of TBME. The temperature is then allowed to rise to room temperature and the mixture is stirred further for 1.5 h. The resulting suspension is then injected with elevated pressure (argon) through a cannula into a second vessel in which a solution of 0.44 ml (5 mmol) of $PCl_3$ in 10 ml of TBME is stirred at −78° C. After the addition, the temperature is allowed to rise to 0° C., and the resulting suspension is stirred further for another 1.5 hours. After adding 10 ml of THF, reaction solution 1 comprising compound 16 is obtained.

c) Preparation of Compound L11:

3.25 ml (5.2 mmol) of n-BuLi (1.6 molar in hexane) are added dropwise at −78° C. with stirring to a solution of 2.31 g (5 mmol) of compound 13 in 10 ml of TBME. The temperature is then allowed to rise to 0° C. and stirred further for 40 minutes. A red reaction solution comprising the lithiated compound 14 is obtained. This is added dropwise at 0° C. with stirring to the reaction solution 1 comprising compound 16. On completion of addition, the cooling is removed and the resulting suspension is stirred overnight. The reaction mixture is hydrolysed with 50 ml of water and 20 ml of saturated aqueous sodium bicarbonate solution, and extracted with methylene chloride. The organic phase is dried over sodium sulphate and the solvent is distilled off on a rotary evaporator. After chromatographic purification (silica gel 60; eluent=2:1 to 1:2 THF/methanol), the desired product L11 is obtained as an orange solid. $^{31}$P NMR ($C_6D_6$, 121 MHz): δ +13.59 (s), −7.81 (s). $^1$H NMR ($C_6D_6$, 300 MHz) characteristic signals: δ 9.04 and 7.39 (two s, 1H), 4.84 (m, 1H), 4.66-4.62 (m, 2H), 4.54 (q, 1H), 4.44 (m, 1H), 4.38 (m, 1H), 4.32 (m, 1H), 4.25 (s, 5H), 4.28-4.21 (m, 2H), 4.13 (m, 1H), 3.96 (m, 1H), 3.92 (m, 1H), 2.19 (s, 6H), 1.12 (d, 3H), 2.1-1.0 (m, 22H).

B) PREPARATION OF METAL COMPLEXES

Example B1

Preparation of an Ir Complex
(COD=Cyclooctadiene)

A solution of 50.2 mg (0.1 mmol) of ligand L1 in 2 ml of methanol is added to a solution of 127.2 mg (0.1 mmol) of [Ir(COD)$_2$]BAr$_F$ in 2 ml of methanol, and the reaction mixture is stirred over 30 minutes. The methanol is removed under reduced pressure and the brown-red residue is washed with pentane. $^{31}$P{H} NMR (161.97 MHz, 300 K, $CD_2Cl_2$): δ=103.1 (d, $J_{PP}$=23.8); 23.4 (d, $J_{PP}$=23.8).

Example B2

Preparation of an Ru Complex

A solution of 50.2 mg (0.1 mmol) of ligand L1 in 2 ml of methanol is added to a solution of 30.6 mg (0.05 mmol) of [RuCl$_2$(p-methylcumene)]$_2$ in 2 ml of methanol, and the reaction mixture is stirred over 30 minutes. The methanol is removed under reduced pressure and the residue is washed with pentane. $^{31}$P{$^1$H} NMR (161.97 MHz, 300 K, MeOH-d$_4$): δ=66.4 (s), 25.9 (s).

Example B3

Preparation of an Rh Complex

A solution of 50.2 mg (0.1 mmol) of ligand L1 in 2 ml of methanol is added to a solution of 30.6 mg (0.05 mmol) of [Rh(COD)$_2$]BAr$_F$ in 2 ml of methanol, and the reaction mixture is stirred over 30 minutes. The methanol is removed under reduced pressure and the residue is washed with pentane. $^{31}$P{$^1$H} NMR (161.97 MHz, 300 K, CDCl$_3$): δ=62.4 (s), 33.4 (d, $^1J_{PRh}$=153 Hz), 23.5 (d, $^2J_{PP}$=23 Hz).

C) USE EXAMPLES

All operations are performed under argon and with degassed solvents.

Example C1

4.73 mg (0.0127 mmol) of [Rh(norbornadiene)$_2$]BF$_4$ and 6.67 mg (0.0133 mmol) of ligand L1 (ratio of ligand to metal=1.05) are stirred in 2 ml of methanol over 10 minutes. A solution of 400 mg (2.5 mmol) of dimethyl itaconate (DMI) in 4 ml of methanol and then sufficient methanol (4 ml) that the substrate concentration is 0.25 M are added to this solution. The argon is drawn off with vacuum and the vessel is connected to a hydrogen supply (1 bar). Switching on the stirrer starts the hydrogenation. After 1 hour, the stirrer is switched off and the solution is placed under argon again. Conversion and enantiomeric excess (ee) are determined by gas chromatography with the aid of a chiral column (Lipodex E): the conversion is complete and the ee is 87%.

Examples C2-C32

The hydrogenations of further substrates, which are compiled in Table 1 below are performed in an analogous manner. The hydrogenations with higher hydrogen pressure are performed in a steel autoclave. In these, the reaction solutions are injected into the argon-purged autoclave with a cannula under an argon countercurrent.

The results are reported in Table 2 below. The abbreviations in Table 1 mean: ee=enantiomeric excess, GC=gas chromatography, TMS=trimethylsilyl, HPLC=high-pressure liquid chromatography.

TABLE 1

| Substrate | Structures | Determination of conversion and ee |
|---|---|---|
| DMI | CH$_2$=C(COOMe)CH$_2$COOMe →$_{H_2}$ CH$_3$CH(COOMe)CH$_2$COOMe | GC with chiral column: Lipodex-E |
| MAA | CH$_2$=C(COOCH$_3$)(NHCOOCH$_3$) →$_{H_2}$ CH$_3$CH(COOCH$_3$)(NHCOOCH$_3$) | GC with chiral column: Chirasil-L-val |
| MAC | PhCH=C(COOMe)(NHCOOCH$_3$) →$_{H_2}$ PhCH$_2$CH(COOMe)(NHCOOCH$_3$) | GC with chiral column: Chirasil-L-val |
| ACA | PhCH=C(COOH)(NHCOOCH$_3$) →$_{H_2}$ PhCH$_2$CH(COOH)(NHCOOCH$_3$) | First derivatization with TMS-diazomethane, then GC with chiral column: Chirasil-L-val |
| MCA | PhCH=C(COOH)(CH$_3$) →$_{H_2}$ PhCH$_2$CH(COOH)(CH$_3$) | First derivatization with TMS-diazomethane, then HPLC with chiral column: Chirasil-OB |

TABLE 1-continued

Substrates

| Substrate | Structures | Determination of conversion and ee |
|---|---|---|
| Z-EAAC | (Z)-ethyl 3-acetamidobut-2-enoate → ethyl 3-acetamidobutanoate | GC with chiral column: Betadex-110 |
| E-EAAC | (E)-ethyl 3-acetamidobut-2-enoate → ethyl 3-acetamidobutanoate | GC with chiral column: Betadex-110 |
| MEA | N-(1-methoxypropan-2-ylidene)-2-ethyl-6-methylaniline → N-(1-methoxypropan-2-yl)-2-ethyl-6-methylaniline | HPLC with chiral column: Chiracel-OD-H |
| EOP | ethyl 3-oxohexanoate → ethyl 3-hydroxyhexanoate | GC with chiral column: Lipodex-E |
| EBAC | ethyl 3-oxo-3-phenylpropanoate → ethyl 3-hydroxy-3-phenylpropanoate | HPLC with chiral column: Chiracel-OD-H |
| MPG | methyl 2-oxo-2-phenylacetate → methyl 2-hydroxy-2-phenylacetate | HPLC with chiral column: Chiracel-OD-J |
| KEPL | 4,4-dimethyldihydrofuran-2,3-dione → 3-hydroxy-4,4-dimethyldihydrofuran-2-one | GC with chiral column: Lipodex-E |

TABLE 2

Hydrogenation results

| No. | Lig. | Metal | Substrate | [S] | S/C | Sol. | P | T | t [h] | C (%) | ee (%) |
|---|---|---|---|---|---|---|---|---|---|---|---|
| C1 | L1 | Rh[a)] | DMI | 0.25 | 200 | MeOH | 1 | 25 | 1 | 100 | 87 |
| C2 | L1 | Rh[a)] | DMI | 0.36 | 100 | THF | 1 | 25 | 14 | 100 | 96.7 |
| C3 | L1 | Rh[a)] | MAA | 0.25 | 200 | MeOH | 1 | 25 | 1 | 100 | 48 |
| C4[1)] | L1 | Ru[e)] | EOP | 0.51 | 1000 | EtOH | 80 | 80 | 16 | 100 | 91 |
| C5 | L1 | Ru[e)] | EBAC | 0.51 | 1000 | EtOH | 80 | 80 | 20 | 100 | 88 |
| C6 | L1 | Rh[a)] | E-EAAC | 0.25 | 100 | EtOH | 1 | 25 | 21 | 100 | 95.6 |
| C7 | L1 | Rh[a)] | E-EAAC | 0.63 | 500 | EtOH | 5 | 25 | 20 | 100 | 95.6 |
| C8 | L1 | Rh[b)] | ACA | 0.1 | 25 | DCE | 1 | 25 | 1 | 100 | 98.6 |
| C9 | L1 | Rh[c)] | KEPL | 0.1 | 25 | toluene | 20 | 25 | 14 | 100 | 88.8 |
| C10 | L2 | Rh[a)] | DMI | 0.25 | 200 | MeOH | 1 | 25 | 1 | 100 | 99.4 |
| C11[2)] | L2 | Ir[d)] | MEA* | 0.25 | 200 | toluene | 80 | 25 | 21 | 100 | 43 |
| C12 | L3 | Rh[a)] | MCA | 0.25 | 200 | MeOH | 5 | 25 | 40 | 91 | 19 |
| C13 | L3 | Rh[b)] | MPG | 0.25 | 200 | toluene | 80 | 25 | 23 | 100 | 21 |
| C14[3)] | L4 | Ru[e)] | EOP | 0.25 | 200 | EtOH | 80 | 80 | 21 | 7 | 68 |
| C15 | L4 | Rh[a)] | MAA | 0.25 | 200 | MeOH | 1 | 25 | 1 | 100 | 98.8 |
| C16 | L4 | Rh[a)] | DMI | 0.25 | 200 | MeOH | 1 | 25 | 2 | 100 | 82.7 |
| C17[3)] | L5 | Ru[e)] | EOP | 0.25 | 200 | EtOH | 80 | 80 | 21 | 30 | 46 |
| C18[3)] | L6 | Ru[e)] | EOP | 0.25 | 200 | EtOH | 80 | 80 | 21 | 100 | 10 |
| C19 | L6 | Rh[a)] | MAA | 0.25 | 200 | MeOH | 1 | 25 | 1 | 100 | 99 |
| C20 | L6 | Rh[a)] | DMI | 0.25 | 200 | MeOH | 1 | 25 | 2 | 100 | 94.9 |
| C21 | L8 | Rh[b)] | MAC | 0.36 | 100 | DCE | 1 | 25 | 2 | 100 | 97.0 |
| C22[4)] | L8 | Rh[b)] | ACA | 0.36 | 100 | DCE | 1 | 25 | 2 | 100 | 88.7 |
| C23 | L8 | Rh[b)] | MAA | 0.36 | 100 | DCE | 1 | 25 | 2 | 100 | 98.8 |
| C24 | L8 | Rh[c)] | ETPY | 0.1 | 25 | toluene | 20 | 25 | 14 | 100 | 72.2 |
| C25 | L8 | Rh[c)] | KEPL | 0.1 | 25 | toluene | 20 | 25 | 14 | 100 | 83.3 |
| C26[5)] | L9 | Ru[f)] | KEPL | 0.1 | 25 | EtOH | 20 | 25 | 14 | 100 | 83.3 |
| C27 | L9 | Rh[c)] | KEPL | 0.1 | 25 | toluene | 20 | 25 | 14 | 100 | 73.2 |
| C28 | L10 | Rh[a)] | MAC | 0.1 | 25 | THF | 1 | 25 | 2 | 100 | 92.1 |
| C29 | L10 | Rh[a)] | MAA | 0.36 | 100 | THF | 1 | 25 | 2 | 100 | 94.3 |
| C30[5)] | L10 | Rh[c)] | KEPL | 0.1 | 25 | toluene | 20 | 25 | 14 | 100 | 87.0 |
| C31 | L11 | Rh[a)] | MAA | 0.25 | 200 | MeOH | 1 | 25 | 1 | 100 | 83.2 |
| C32 | L11 | Rh[a)] | DMI | 0.25 | 200 | MeOH | 1 | 25 | 1 | 100 | 94.5 |

Additions:
[1)] 1N HCl (1.2% based on solvent volume);
[2)] 2 equivalents of tetrabutyl-ammonium iodide/Ir and CF$_3$COOH (0.6% based on solvent volume);
[3)] 1N HCl (0.6% based on solvent volume);
[4)] 12 equivalents if 1,4-diazobicyclo[2.2.2]octane/Ir;
[5)] 4 equivalents of 1,4-diazobicyclo[2.2.2]octane/Ir
In the table:
[S] means molar substrate concentration;
S/C means substrate/catalyst ratio;
t means hydrogenation time;
Lig. means ligand,
Sol. means solvent (MeOH = methanol; EtOH = ethanol; Tol = toluene; THF = tetrahydrofuran; DCE = 1,2-dichloroethane);
Metal means metal precursor which is used in the hydrogenations:
Rh[a)] = [Rh(norbornadiene)$_2$]BF$_4$;
Rh[b)] = [Rh(cyclooctadiene)Cl]$_2$;
Rh[c)] = [Rh(norbornadiene)triflate]$_2$;
[Ir[d)] = [Ir(cyclooctadiene)Cl]$_2$;
Ru[e)] = [RuI$_2$(p-methyl-cumene)]$_2$;
Ru[f)] = [RuCl$_2$(p-methylcumene)]$_2$;
Lig. = ligand,
C = conversion;
Conf. = configuration.

The invention claimed is:

1. A compound of the formula I having at least two chiral centres in the form of mixtures of diastereomers or pure diastereomers secondary phosphine-Q-P*(=O)HR$_1$    (I), in which
secondary phosphine is a secondary phosphine group with hydrocarbon radicals or heterohydrocarbon radicals as substituents;
Q is a bivalent bisaryl or bisheteroaryl radical with an axial chiral centre to which the two phosphorus atoms are bonded in the ortho positions to the bisaryl or bisheteroaryl bridge bond,
or Q is a bivalent ferrocenyl radical with a planar chiral centre, or Q is a bivalent ferrocenyl radical without a planar chiral centre, to which the phosphorus atom of the secondary phosphine is bonded directly or via a $C_1$-$C_4$- carbon chain to a cyclopentadienyl ring,
the —P*(=O)HR$_1$ group is bonded either on the same cyclopentadienyl ring in ortho position to the bonded secondary phosphine or on the other cyclopentadienyl ring;
P* is a chiral phosphorus atom, and
R$_1$ is a hydrocarbon radical, a heterohydrocarbon radical or a ferrocenyl radical,
where R$_1$ is a ferrocenyl radical with a planar chiral centre when Q as a bivalent ferrocenyl radical does not have a planar chiral centre.

2. A compound according to claim 1, wherein R$_1$ is a hydrocarbon radical selected from the group of linear or branched $C_1$-$C_{18}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl, naphthyl, furyl or benzyl; or halogen-, $C_1$-$C_6$-alkyl-, trifluoromethyl-, $C_1$-$C_6$-alkoxy-, trifluoromethoxy-, $(C_6H_5)_3Si$—, $(C_1$-$C_{12}$-alkyl$)_3Si$—, or secondary amino-substituted phenyl, naphthyl, furyl or benzyl, or $R_1$ is an unsubstituted or mono- or polysubstituted ferrocenyl radical.

3. A compound according to claim 1, wherein the secondary phosphine corresponds to the formula —$PR_2R_3$ in which $R_2$ and $R_3$ are each independently a hydrocarbon radical which has 1 to 18 carbon atoms and is unsubstituted or substituted by $C_1$-$C_6$-alkyl, trifluoromethyl, $C_1$-$C_6$-alkoxy, trifluoromethoxy, $(C_1$-$C_4$-alkyl$)_2$-amino, $(C_6H_5)_3Si$, $(C_1$-$C_{12}$-alkyl$)_3Si$, halogen, and/or O heteroatoms.

4. A compound according to claim 1, wherein Q in formula I represents radicals in which two hydrocarbon aromatics, two heteroaromatics or one hydrocarbon aromatic and one heteroaromatic are joined to one another.

5. A compound according to claim 1, which corresponds to the formulae IIIa, VIIa, VIIIa, IXa or XXa

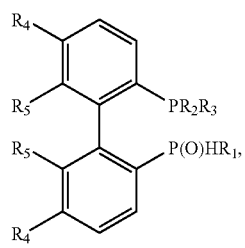

(IIIa)

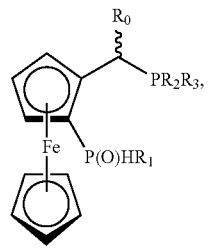

(VIIa)

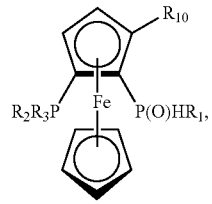

(VIIIa)

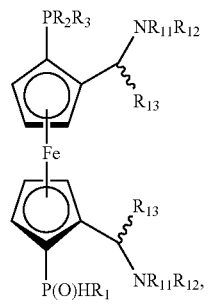

(IXa)

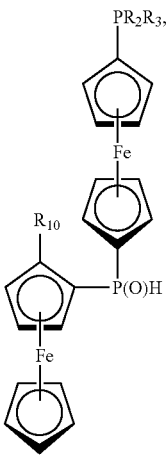

(XXa)

in which
the 3,3' and/or 4,4' positions in formula IIIa may be substituted by $C_1$-$C_4$-alkyl, $C_1$-$C_4$-alkoxy, trifluoromethyl or trimethylsilyl;
$R_1$ is $C_1$-$C_8$-alkyl, unsubstituted cyclopentyl or cyclohexyl or cyclopentyl or cyclohexyl substituted by 1 to 3 $C_1$-$C_4$-alkyl or $C_1$-$C_4$-alkoxy, or benzyl and phenyl which are unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl;
$R_2$ and $R_3$ are each independently a hydrocarbon radical which has 1 to 18 carbon atoms and is unsubstituted or substituted by $C_1$-$C_6$-alkyl, trifluoromethyl, $C_1$-$C_6$-alkoxy, trifluoromethoxy, $(C_1$-$C_4$-alkyl$)_2$-amino, $(C_6H_5)_3Si$, $(C_1$-$C_{12}$-alkyl$)_3Si$, halogen, and/or O heteroatoms;
$R_4$ is hydrogen or independently as defined for $R_5$;
$R_5$ is $C_1$-$C_4$-alkyl, $C_1$-$C_4$-alkoxy, $C_1$-$C_4$-hydroxyalkyl, $C_2$-$C_4$-hydroxyalkoxy, $C_1$-$C_4$-alkoxy-$C_1$-$C_2$-alkyl, $C_1$-$C_4$-alkoxy-$C_1$-$C_2$-alkoxy, trifluoromethyl or trimethylsilyl, or $R_4$ and $R_5$ together are —CH=CH—CH=CH—, trimethylene, tetramethylene, —O—$CH_2$—O—, —O—$CF_2$—O—, —O—$CH_2$—$CH_2$—O—, —N(methyl)-$CH_2$—$CH_2$—O—;
the $R_5$ radicals together are $C_2$-$C_6$-alkylene, —O—($C_1$-$C_4$-alkylene)-O— or —O—$CF_2$—O—;
$R_9$ is $C_1$-$C_4$-alkyl, cyclopentyl, cyclohexyl, phenyl, methylphenyl, methylbenzyl or benzyl;
$R_{10}$ is —$CH_2$—$NR_{11}R_{12}$, —$CHR_9$—$NR_{11}R_{12}$, vinyl, methyl or ethyl; and
$R_{11}$ and $R_{12}$ are identical radicals, and $R_{11}$ and $R_{12}$ are each $C_1$-$C_4$-alkyl, cyclopentyl, cyclohexyl, phenyl, methylphenyl, methylbenzyl or benzyl, or $R_{11}$ and $R_{12}$ together are tetramethylene or 3-oxapentane-1,5-diyl; and
the $R_{13}$ are each $C_1$-$C_4$-alkyl, cyclopentyl, cyclohexyl, phenyl, methylphenyl, methylbenzyl or benzyl.

6. A process for preparing a compound of the formula I in claim 1, which comprises reacting a compound of the formula X secondary phosphine-Q-Hal (X)

in which secondary phosphine and Q are each as defined in claim 1 and Hal is Cl, Br or I with a metallating reagent and thereafter with a halophosphine of the formula XI Hal-$PX_2R_1$ (XI), in which
R₁ is as defined in formula I,
Hal is Cl, Br or I, and
X₂ is Cl, Br, I, $C_1$-$C_4$-alkoxy or ($C_1$-$C_4$-alkyl)₂-amino,
to form a compound of the formula XII $$\text{secondary phosphine-Q-PX}_2\text{R}_1 \tag{XII}$$

and hydrolyzing the compound of formula XII with water to give a compound of the formula I.

7. A metal complex of a transition metal of a transition group of the Periodic Table of the Elements with a compound of the formula I of claim 1 as a ligand.

8. A process for preparing a chiral organic compound by asymmetric addition of hydrogen to a carbon or carbon-heteroatom double bond in a prochiral organic compound in the presence of a catalyst, which comprises performing the addition is in the presence of a catalytic amount of at least one metal complex according to claim 7.

9. A method for asymmetric addition of hydrogen to a carbon or carbon-heteroatom double bond in a prochiral organic compound for preparing a chiral organic compound, which performing the addition in the presence of 0.00001 to 10 mol %, based on the prochiral organic compound to be hydrogenated, of the metal complex according to claim 8 as homogenous catalyst.

* * * * *